US008993633B2

(12) United States Patent
Megeney et al.

(10) Patent No.: US 8,993,633 B2
(45) Date of Patent: Mar. 31, 2015

(54) TREATMENT OF MUSCLE DISEASE CHARACTERIZED BY INSULIN RESISTANCE

(75) Inventors: Lynn Megeney, Ottawa (CA); Carol Evans, Ottawa (CA)

(73) Assignees: Fate Therapeutics, (Canada) Inc., San Diego, CA (US); Ottaw Hospital Research Institute, Ottawa (CA)

( * ) Notice: Subject to any disclaimer, the term of this patent is extended or adjusted under 35 U.S.C. 154(b) by 0 days.

(21) Appl. No.: 13/320,906

(22) PCT Filed: May 18, 2010

(86) PCT No.: PCT/CA2010/000734
§ 371 (c)(1),
(2), (4) Date: Nov. 16, 2011

(87) PCT Pub. No.: WO2010/132982
PCT Pub. Date: Nov. 25, 2010

(65) Prior Publication Data
US 2012/0065176 A1 Mar. 15, 2012

Related U.S. Application Data

(60) Provisional application No. 61/244,669, filed on Sep. 22, 2009, provisional application No. 61/179,040, filed on May 18, 2009.

(51) Int. Cl.
*A61K 31/155* (2006.01)
*A61K 31/573* (2006.01)
*A61P 21/00* (2006.01)
*C07C 313/30* (2006.01)
*C07F 9/6571* (2006.01)

(52) U.S. Cl.
CPC ............. *C07C 313/30* (2013.01); *A61K 31/155* (2013.01); *C07F 9/657154* (2013.01); *C07C 2101/14* (2013.01); *G01N 2333/62* (2013.01); *G01N 2800/10* (2013.01); *G01N 2800/52* (2013.01)
USPC ............ 514/635; 514/171; 564/233; 552/559

(58) Field of Classification Search
CPC .. C07C 279/26; C07C 49/617; A61K 31/155; A61K 31/573; A61K 31/57; Y10S 514/907
USPC .................... 514/635, 171; 564/233; 552/559
See application file for complete search history.

(56) References Cited

U.S. PATENT DOCUMENTS 3,147,271 A 9/1964 Shapiro et al.
3,152,181 A 10/1964 Shapiro et al.
3,366,650 A 1/1968 Bernstein et al.
3,531,484 A 9/1970 Bicking et al.
5,434,142 A 7/1995 Antoku et al.

FOREIGN PATENT DOCUMENTS

GB 607720 9/1948
WO WO/2007/134867 11/2007

OTHER PUBLICATIONS

Huttunen et al. J. Pharm. Biomed. Analysis 2009, 50(3), 469-474.*
Definition of Prevent, Princeton University "About WordNet." WordNet. Princeton University. 2010. <http://wordnet.princeton.edu>, downloaded from internet on Sep. 18, 2012.*
Bushby et al. Lancet Neurol. 2010, 9(1), 77-93.*
Rutter et al. Neuromuscular Disorders 2009, 19, 612, Abstract of Poster presentation, Pediatric Academic Societies Annual Meeting, Baltimore, May 2-5, 2009.*
Stepensky et al. Drug metabolism and disposition 2002, 30 (8), 861-868 Cleasby et al. Diabetes 2004, 53, 3258-3266.*
Rutter et al. Poster presentation, Pediatric Academic Societies Annual Meeting, Baltimore, May 2-5, 2009, Abstract No. 3854.50, in Pediatric Academic Societies' 2000-2013 Archive Abstracts2View [Online], http://www.abstracts2view.com/pasall/view.php?nu=PAS09L1_3254 (accessed Apr. 22, 2014).*
International Search Report for International Application No. PCT/CA2010/00734, mailed on Jul. 28, 2010.
International Preliminary Report on Patentability for PCT/CA2010/000734, dated Nov. 22, 2011.
Written Opinion for PCT/CA2010/000734, dated Jul. 22, 2010.
Abe et al., "Dramatic Improvement of Blood Glucose Control after Pioglitazone Treatment in Poorly Controlled Over-weight Diabetic Patients with Myotonic Dystrophy," *Endocrine Journal*,56(7):911-913, 2009.
Abramovici et al., "Diacylglycerol Kinase-Localization in Skeletal Muscle Is Regulated by Phosphorylation and Interaction with Syntrophins," *Molecular Biology of the Cell*, 14:4499-4511, Nov. 2003.

(Continued)

*Primary Examiner* — Sreeni Padmanabhan
*Assistant Examiner* — Irina Neagu
(74) *Attorney, Agent, or Firm* — Cooley LLP

(57) ABSTRACT

It is reported herein that certain muscle diseases and conditions, including forms of muscular dystrophy, are characterized by impaired insulin-dependent signaling in the muscle tissue, in essence, a form of insulin resistance. The present disclosure relates to therapeutic agents, compositions and methods for treating a muscle disease or condition characterized by impaired insulin-dependent signaling by targeting components of the defective insulin signaling pathway. The disease or condition may be treated by administering a therapeutic agent that activates the insulin signaling pathway, in particular, therapeutic agents that act post-insulin receptor to modulate intracellular effector molecules. An exemplary modulator is metformin. Metformin may be administered alone or may be co¬ administered with another therapeutic agent for treating the muscle disease or condition, such as a corticosteroid.

8 Claims, 11 Drawing Sheets

(56) References Cited

OTHER PUBLICATIONS

Aguirre et al., "The c-Jun NH2-terminal Kinase Promotes Insulin Resistance during Association with Insulin Receptor Substrate-1 and Phosphorylation of Ser$^{307}$," *Journal of Biological Chemistry*, 275:12:9047-9054, 2000.
Ainley et al., "Synthetic Antimalarials. Part XXXIII. An Alternative Route to N1-Aryl-N5-Alkyldiguanides and Related Compounds: the Condensation of Guanidines and Cyananides," *J. Chem. Soc.*, 98-106, 1949.
Angelini, "The Role of Corticosteroids in Muscular Dystrophy: A Critical Appraisal," *Muscle & Nerve*, 36:424-435, 2007.
Asakura, "Myogenic specification of side population cells in skeletal muscle," *J Cell Biol.*, 159:123-134, 2000.
Barton et al, "Muscle-specific expression of insulin-like growth factor I counters muscle decline in mdx mice; *Journal of Cell Biology*," 157:137-147, 2002.
Barton, "The ABCs of IGF-I isoforms: impact on muscle hypertrophy and implications for repair," *Appl. Physiol. Nutr. Metab.*, 31: 791-797, 2006.
Blaauw et al., "Akt activation prevents the force drop induced by eccentric contractions in dystrophin-deficient skeletal muscle," *Human Molecular Genetics*, 17:23 3686-3696, 2008.
Bonnemann et al., "Beyond dystrophin: current progress in the muscular dystrophies," *Curr. Opin. Ped.*, 8:569-582, 1996.
Brown, "Dystrophin-Associated Proteins and the Muscular Dystrophies," *Annu. Rev. Med.*, 48:457-66, 1997.
Chakkalakal et al., "Stimulation of calcineurin signaling attenuates the dystrophic pathology in mdx mice," *Human Molecular Genetics*, 13:(4) 379-388, 2004.
Chakkalakal et al; Molecular, cellular, and pharmacological therapies for Duchenne/Becker muscular dystrophies; *FASEB J*, 19, 880-891. Review. 2005.
Chakkalakal et al., "Targeted inhibition of Ca21/calmodulin signaling exacerbates the dystrophic phenotype in mdx mouse muscle," *Human Molecular Genetics*, 15(9):1423-1435, 2006.
Chen et al., "Expression Profiling in the Muscular Dystrophies: Identification of Novel Aspects of Molecular Pathophysiology," *Journal of Cell Biology*, 151(6):1321-1336, 2000.
Chin et al., "A calcineurin-dependent transcriptional pathway controls skeletal muscle fiber type," *Genes Dev.*, 12:2499-2509, 1998.
Cho D. H. and Tapscott S. J., "Myotonic dystrophy: Emerging mechanisms for DM1 and DM2," *Biochimica et Biophysica Acta*, 1772:195-204, 2007.
Chung et al., "HSP72 protects against obesity-induced insulin resistance," *Proc Natl Acad Sci USA*, 105:1739-1744, 2008.
Cohen et al., "Effects of insulin-sensitising agents in mice with hepatic insulin resistance," *Diabetologia*,47:407-411, 2004.
Colautti A. and Maurich V., "R-Benzensulfonilbiguanidi—Di Possible Interesse," *Biologico; Il Farmaco*, 26(9):850-856, 1971.
Duan et al., "Synthesis and Study of Antidiabetic Properties of the Neodymium Complexes with N5-[o-(un)Substituted Benzoyl]-N1,N1-dimethylbiguanide," *Chinese Journal of Chemistry*, 25:1919-1923, 2007.
Ervasti J. M. and Sonnemann K. J., "Biology of the Striated Muscle Dystrophin-Glycoprotein Complex," *Int Rev Cytol.* 265:191-225, 2008.
Even et al., "Defective regulation of energy metabolism in mdx-mouse skeletal muscles," *Biochem. J.*304:649-654, 1994.
Fisher J. and Upadhyaya M., "Molecular genetics of facioscapulohumeral muscular dystrophy (FSHD)," *Neuromuscular Disorders*, 7:55_62, 1997.
Freund et al., "Duchenne and Becker Muscular Dystrophy—A molecular and immunohistochemical approach," *Arq Neuropsiquiatr*, 65(1):73-76, 2007.
Funakoshi et al., "Emerin and cardiomyopathy in Emery-Dreifuss muscular dystrophy," *Neuromuscular Disorders* 9:108-114, 1999.
Gregorevic et al., "Administration of Insulin-Like Growth Factor-I Improves Fatigue Resistance of Skeletal Muscles from Dystrophic mdx Mice," *Muscle Nerve* 30:295-304, 2004.

Guglieri et al., "Limb-girdle muscular dystrophies," *Current Opinion in Neurology*, 21:576-584, 2008.
Han, "Targeted Prodrug Design to Optimize Drug Delivery," *AAPS Pharmsci*, 2000; 2(1):6, 2000.
Hasegawa et al., "Stress-activated Protein Kinase-3 Interacts with the PDZ Domain of a1-Syntrophin," *J Biol Chem*, 274:12626-12631, 1999.
Hilder et al., "Phosphorylation of insulin receptor substrate-1 serine 307 correlates with JNK activity in atrophic skeletal muscle," *FEBS Letters*, 553:63-67, 2003.
Hirosumi et al., "A central role for JNK in obesity and insulin resistance," *Nature*, 420:333-336, 2002.
Hoffman et al., "Characterization of Dystrophin in Muscular-Biopsy Specimens from Patients with Duchenne's or Becker's Muscular Dystrophy," *New England Journal of Medicine*, 318:1363-1368, 1988.
Huttunen et al., "Towards Metformin Prodrugs," *Synthesis*, 22:3619-3624, 2008.
Huttunen et al., "Determination of metformin and its prodrugs in human and rat blood by hydrophilic interaction liquid chromatography," *Journal of Pharmaceutical and Biomedical Analysis*, 50:469-474, 2009.
Huttunen et al, "The First Bioreversible Prodrug of Metformin with Improved Lipophilicity and Enanced Intestinal Absorption," *J. Med. Chem.*, 52:4142-4148, 2009.
Khairallah et al., "Metabolic and signaling alterations in dystrophin-deficient hearts precede overt cardiomyopathy," *Journal of Molecular and Cellular Cardiology*, 43:119-129, 2007.
Khan, "Corticosteroid therapy in Duchenne muscular dystrophy," *J. Neurol. Sci.*, 120:8-14, 1993.
Kolodziejczyk et al., "Activation of JNK1 contributes to dystrophic muscle pathogenesis," Current Biology, 11:1278-1282, 2001.
Kouki et al., "Low-dose metformin improves hyperglycaemia related to myotonic dystrophy," *Diabetic Medicine*, 22:346-347, 2005.
Langenbach K. J. and Rando T. A.; Inhibition of Dystroglycan Binding to Laminin Disrupts the PI3K/AKT Pathway and Survival Signaling in Muscle Cells; Muscle Nerve 26: 644-653, 2002.
Lim L. E. and Campbell K. P., "The sarcoglycan complex in limb-girdle muscular dystrophy," *Curr. opin. Neurol.*, 11(5):443-452, 1998.
Liquori et al.; Myotonic Dystrophy Type 2 Caused by a CCTG Expansion in Intron 1 of ZNF9; Science, 2001 3; 293(5531): 864-7.
Liu et al., "The antidiabetic effects of cysteinyl metformin, a newly synthesized agent, in alloxan- and streptozocin-induced diabetic rats," *Chemico-Biological Interactions*,173:68-75, 2008.
Lizcano J. M. and Alessi D. R., "The insulin signalling pathway," *Current Biology*, 12:236-238, 2002.
Lumeng et al., "Interactions between b2-syntrophin and a family of microtubuleassociated serine/threonine kinases," *Nat Neurosci.* 2:611-617, 1999.
Madhavan, R. and Jarrett, H. W.; Electrochemical and Functional Characterization of the Proline Dehydrogenase Domain of the PutA Flavoprotein from *Escherichia coli*; Biochemistry 2002, 41, 6525-6532.
Madhavan, R. and Jarrett, H. W., "Phosphorylation of dystrophin and K-syntrophin by Ca2‡-calmodulin dependent protein kinase II," *Biochimica et Biophysica Acta* 1434:260-274, 1999.
Megeney et al., "MyoD is required for myogenic stem cell function in adult skeletal muscle," *Genes & Development*, 10:1173-1183, 1996.
Misra; AMP activated protein kinase: a next generation target for total metabolic control; Expert Opin. Ther. Targets (2008) 12(1):91-100.
Mokhtarian et al., "Components of energy expenditure in the mdx mouse model of Duchenne muscular dystrophy," *Pflfigers Arch-Eur J Physiol*,431:527-532, 1996.
Musaro et al., "IGF-1 induces skeletal myocyte hypertrophy through calcineurin in association withGATA-2 and NF-ATc1," *Nature*, 400:581-585, 1999.
Musi N. and Goodyear L. J., "Metformin Increases AMP-Activated Protein Kinase Activity in Skeletal Muscle of Subjects With Type 2 Diabetes," *Diabetes*, 51:581-585, 2002.
Musi N. and Goodyear .L J., "Insulin Resistance and Improvements in Signal Transduction," *Endocrine*, 29:73-80, 2006.

(56) References Cited

OTHER PUBLICATIONS

Naya et al., "Stimulation of Slow Skeletal Muscle Fiber Gene Expression by Calcineurin in Vivo," *J Biol Chem.*, 275:4545-4548, 2000.

Noguchi, "The biological function of insulin-like growth factor-1 in myogenesis and its therapeutic effect on muscular dystrophy," *Acta Myologica*, 24:115-118, 2005.

Peter et al., "Myogenic Akt signaling upregulates the utrophin-glycoprotein complex and promotes sarcolemma stability in muscular dystrophy," *Hum Mol Genet.*, 18:318-327, 2009.

Petrof et al., "Dystrophin protects the sarcolemma from stresses developed A87during muscle contraction," *Proc. Natl. Acad. Sci.*,90:3710-3714, 1993.

Piccardo et al., "Insulin Resistance in Myotonic Dystrophy," *Enzymbe*, 45:14-22, 1991.

Runti et al., "Potenziali Antivirali," *Il Farmaco*, 23: 827-841, 1979.

St-Pierre et al., "Glucocorticoid treatment alleviates dystrophic myofiber pathology by activation of the calcineurin/NF-AT pathway," *The FASEB Journal*, 18:1937-1939, 2004.

Sandri et al., "Foxo Transcription Factors Induce the Atrophy-Related Ubiquitin Ligase Atrogin-1 and Cause Skeletal Muscle Atrophy," *Cell*, 117:399-412, 2004.

Semsarian et al., "Skeletalmusclehypertrophyis mediated by aCa2+-dependent calcineurin signalling pathway," *Nature*, 400:576-581, 1999.

Sewry, "Pathological defects in congenital myopathies," *J Muscle Res Cell Motil*,29:231-238, 2008.

Schertzer JD and Lynch GS, "Comparative evaluation of IGF-I gene transfer and IGF-I protein administration for enhancing skeletal muscle regeneration after injury," *Gene Therapy*,13, 1657-1664, 2006.

Schertzer et al., "Systemic administration of IGF-I enhances oxidative status and reduces contraction-induced injury in skeletal muscles of mdx dystrophic mice," *Am J Physiol Endocrinol Metab*, 291: E499-E505, 2006.

Shapiro et al., "Hypoglycemic Agents. IV. 1-3 $N^1$,$N^5$-Alkyl- and Aralkylbiguanides," *J. Am. Chem. Soc.*, 81: 4635-4639, 1959.

Sharp et al., "An Error in Dystrophin mRNA Processing in Golden Retriever Muscular Dystrophy, an Animal Homologue of Duchenne Muscular Dystrophy," *Genomics*, 13:115-121, 1992.

Srinivas et al., "Studies in Synthetic Antimalarials, Part XX. Some Suphabiguanide Derivatives," *J Indian Inst. Sci.*,35A:47-54, 1953.

Stebbins et al., "Identification of a new JNK inhibitor targeting the JNK-JIP interaction site," *PNAS*, 105(43):16809-16813, 2008.

Stitt et al., "The IGF-1/PI3K/Akt Pathway Prevents Expression of Muscle Atrophy-Induced Ubiquitin Ligases by Inhibiting FOXO Transcription Factors," *Molecular Cell*, 14:395-403, 2004.

Stupka et al., "Activated calcineurin ameliorates contraction-induced injury to skeletal muscles of mdx dystrophic mice," *J Physiol*, 575. 2:645-656, 2006.

Stupka et al., "Stimulation of calcineurin A activity attenuates muscle pathophysiology in mdx dystrophic mice," *Am J Physiol Regul Integr Comp Physiol*, 294:R983-R992, 2008.

Suwa et al.; Metformin increases the PGC-1 protein and oxidative enzyme activities possibly via AMPK phosphorylation in skeletal muscle in vivo; J Appl Physiol 101: 1685-1692, 2006.

Tawil, "Facioscapulohumeral Muscular Dystrophy," *Neurotherapeutics*; 5(4):601-6, 2008.

Vainzof et al., "Animal Models for Genetic Neuromuscular Diseases," *J Mol Neurosci*,34:241-248, 2008.

Voit; Congenital muscular dystrophies: 1997 update; Brain & Development 20 (1998) 65-74.

Willmann et al.; Mammalian animal models for Duchenne muscular dystrophy; Neuromuscular Disorders 19 (2009) 241-249.

Worton; Muscular Dystrophies: Diseases of the Dystrophin-Glycoprotein; Science; 270: 755-756 (1995).

Wu et al., "MEF2 responds to multiple calcium-regulated signals in the control of skeletal muscle fiber type," *EMBO J.*, 19 1963-1973, 2000.

Yang et al., "SH3 Domain-mediated Interaction of Dystroglycan and Grb2," *J Biol Chem.*, 270:11711-11714,1995.

Zhou et al., "Role of AMP-activated protein kinase in mechanism of metformin action," *J. Clin. Invest.*, 108:1167-1174, 2001.

\* cited by examiner

A)

B)

A)

B)

TREATMENT OF MUSCLE DISEASE CHARACTERIZED BY INSULIN RESISTANCE

TECHNICAL FIELD

The present disclosure relates generally to therapeutic agents, compositions and methods for treating muscle diseases and conditions characterized by impaired insulin-dependent signaling in muscle tissue, in essence, a form of insulin resistance.

BACKGROUND

There are numerous diseases and conditions that affect muscle. Examples include muscle wasting diseases, including cachexia, muscle attenuation or atrophy, including sarcopenia, ICU-induced weakness, surgery-induced weakness, neuromuscular diseases, and muscle degenerative diseases, such as muscular dystrophies.

Muscular dystrophy (MD) refers to a group of hereditary, progressive, degenerative disorders characterized by progressive muscle weakness, defects in muscle proteins, and the destruction of muscle fibers and tissue over time. In many cases, the histological picture shows variation in fiber size, muscle cell necrosis and regeneration, and often proliferation of connective and adipose tissue. The diseases primarily target the skeletal or voluntary muscles. However, muscles of the heart and other involuntary muscles are also affected in certain forms of muscular dystrophy.

There are several forms of muscular dystrophy, which differ in their age of onset, penetrance, severity, and pattern of muscles affected. Known forms of muscular dystrophy include Duchenne muscular dystrophy (DMD), Becker muscular dystrophy (BMD), Limb-Girdle muscular dystrophies, myotonic dystrophy (Steinert's disease), Emery-Dreifuss muscular dystrophy, Landouzy-Dejerine muscular dystrophy, facioscapulohumeral muscular dystrophy (FSH), von Graefe-Fuchs muscular dystrophy, oculopharyngeal muscular dystrophy (OPMD), distal muscular dystrophy, and congenital muscular dystrophies. While these are the main forms classified as muscular dystrophy, there are more than 100 diseases in total with similarities to muscular dystrophy. Some dystrophies may result from different underlying defects than others. Most types of MD are multi-system disorders with manifestations in body systems including the musculoskeletal, gastrointestinal and nervous systems, the heart, endocrine glands, skin, eyes and other organs.

Duchenne Muscular Dystrophy (DMD) is the most common inherited lethal childhood muscular dystrophy, affecting about 1 in 3000 males. Children with DMD usually become wheelchair bound by the age of 11 or 12 years and affected individuals usually die in the second or third decade of life. DMD originates from mutations in the dystrophin gene located on the X chromosome (Xp21), leading to loss of dystrophin protein with attendant muscle fiber destruction. Although the role of the dystrophin protein in maintaining skeletal myofiber integrity is generally well recognized, the exact mechanism that leads to myofiber destruction and loss in dystrophic muscle is not well understood. The discovery of the dystrophin gene and the subsequent characterization of the protein product have established dystrophin as an integral sarcolemmal protein, linking the muscle sarcomere and cytoskeleton to the surrounding extracellular matrix. The localization of dystrophin is synonymous with maintaining muscle integrity and its absence (as evidenced in DMD) leads to membrane fragility, contraction induced myofiber damage, and death (Petrof et al. 1993).

Becker type muscular dystrophy (BMD), also known as Benign pseudohypertrophic muscular dystrophy is an X-linked recessive inherited disorder characterized by slowly progressive muscle weakness of the legs and pelvis, which is also caused by mutations in the dystrophin gene, has onset in adolescence or adulthood with a less severe course of progression. BMD is related to Duchenne Muscular Dystrophy in that both result from a mutation in the dystrophin gene, but in DMD no functional dystrophin is produced making DMD much more severe than BMD. Both DMD and BMD have traditionally been called "X-linked" recessive diseases (Freund et al., 2007).

The limb girdle muscular dystrophies all show a similar distribution of muscle weakness, affecting both upper arms and legs. Many forms of limb girdle muscular dystrophy have been identified, showing different patterns of inheritance: autosomal recessive (designated LGMD1) or autosomal dominant (LGMD2). In an autosomal recessive pattern of inheritance, an individual receives two copies of the defective gene, one from each parent. In an autosomal dominant disease, the disorder can occur in either sex when an individual inherits a single defective gene from either parent. The recessive limb girdle muscular dystrophies are more frequent than the dominant forms, and may be more severe. Limb girdle muscular dystrophy can have a childhood onset, although more often symptoms appear in adolescence or young adulthood. The dominant limb girdle muscular dystrophies usually show adult onset. Some of the recessive forms have been associated with defects in proteins that make up the dystrophin-glycoprotein complex. Mutations in one component of the dystrophin-glycoprotein complex, the sarcoglycans, can lead to the forms of limb girdle muscular dystrophy known as LGMD2C, 2D, 2E, and 2F. Defects in caveolin 3, a protein that associates with the dystrophin-glycoprotein complex, lead to LGMD1C, while mutations in dysferlin, a protein that is thought to interact with caveolin 3, cause LGMD2B. Mutations in genes not related to the dystrophin-glycoprotein complex are implicated in other forms of limb girdle muscular dystrophy. For example, mutations in the enzymatic protein calpain 3 lead to LGMD2A (Guglieri M. et al., 2008).

Myotonic dystrophy is the most common form of muscular dystrophy. It is dominantly inherited and characterized by muscle hyperexcitability (myotonia), muscle wasting and weakness, cataracts, hypogonadism, cardiac conduction abnormalities and other developmental and degenerative manifestations frequently including cognitive dysfunction. Penetrance can be variable. Myotonic dystrophy can be caused by mutations in different genes, but the characteristics are quite similar. Type 1 myotonic dystrophy (DM1) is caused by expansion of a CTG triplet repeat in an untranslated region of the dystrophia myotonica protein kinase gene (DMPK) on chromosome 19, while type 2 (DM2) is caused by expansion of a CCTG repeat in the first intron of the zinc finger protein-9 gene (ZNF9) on chromosome 3. Repeat number in the myotonic dystrophies increases in subsequent generations (anticipation). DM1 also has congenital and childhood onset forms; these early appearing forms of the disease differ mechanistically from the adult form only in exhibiting larger CTG repeats that, in turn, trigger earlier appearance of symptoms. Those patients that survive early onset DM1 frequently exhibit morbidity and mortality in the third and fourth decades relating to cardiopulmonary involvement (Liguori C L. et al., 2001; Cho D H. et al., 2007).

Facioscapulohumeral muscular dystrophy (FSHD), a dominantly inherited disorder, is the third most common dystrophy after Duchenne and myotonic muscular dystrophy. FSHD is an autosomal dominant progressive degenerative disease that initially affects the muscles of the face (facio), shoulders (scapulo), and upper arms (humeral), followed by the muscles of the feet, pelvic girdle, and abdomen. Affected individuals may also suffer from hearing loss. Onset and progression of the disease is variable and often the weakness is asymmetrical in affected individuals. Life expectancy is typically within normal range, but the disease can lead to severe disability. Nearly all cases are associated with deletions of tandem repeats, termed D4Z4, in a distal region of chromosome 4 (4q35) (Tawil R., 2008).

The congenital muscular dystrophies are a heterogeneous class of disorders, and include several disorders with a range of symptoms. Muscle degeneration can be mild or severe, and may be restricted to skeletal muscle, or paired with effects on the brain and other organs. Defects in the protein merosin are responsible for about half of the cases in the U.S. Mutations in one of the integrin proteins gives rise to another form of congenital muscular dystrophy. Defects in the proteins called fukutin and fukutin-related protein cause the most common forms of congenital muscular dystrophy found in Japan. All of these proteins are thought to have some relationship to the dystrophin-glycoprotein complex. Some forms of congenital muscular dystrophy, including Fukuyama muscular dystrophy, muscle-eye brain disease, and Walker-Warburg syndrome are due to defective glycosylation of one of the proteins in the dystrophin-glycoprotein complex (alpha-dystroglycan) and show severe brain malformations, such as lissencephaly (a "cobblestone" appearance to part of the brain) and hydrocephalus (an excessive accumulation of fluid in the brain). Other forms, including the merosin-absent form and rigid spine syndrome, do not have major brain malformations associated with the disease. The molecular basis for many forms of congenital muscular dystrophy remains unknown (Sewry Calif., 2008).

Several other forms of muscular dystrophy also occur. Oculopharyngeal muscular dystrophy, which causes weakness in the eye, throat, and facial muscles, followed by pelvic and shoulder muscle weakness, has been attributed to a short triplet repeat expansion in the nuclear polyadenylate binding protein 1 gene (PABPN1), a gene involved in translating the genetic code into functional proteins. Inheritance follows either autosomal dominant or autosomal recessive patterns.

Polyalanine tract expansion from a norm of 10 to 12-17 residues causes aggregation of filamentous intranuclear inclusions in skeletal muscle which appear to precipitate the disease. This disease is most common in people of French-Canadian descent or people of Hispanic descent from certain regions of the Southwest. Miyoshi myopathy, one of the distal muscular dystrophies, causes initial weakness in the calf muscles, and is caused by defects in the protein dysferlin, which is the same gene responsible for LGMD2B, reinforcing the idea that progress against one form of muscular dystrophy should be informative to other forms. There are two forms of Emery-Dreifuss muscular dystrophy, an X-linked and an autosomal dominant form. Emery-Dreifuss muscular dystrophy is characterized by weakness in the shoulder girdle and lower legs, as well as the development of contractures in regions of the body, particularly the elbows, Achilles tendons, and neck. Defects in proteins that make up the nucleus, including emerin, and lamin A/C, are implicated in the disorder.

Several animal models, manifesting phenotypes observed in neuromuscular diseases, have been identified in nature or generated in laboratory. These models generally present physiological alterations observed in human patients and can be used as important tools for genetic, therapeutic, and histopathological studies. The study of animal models for genetic diseases, in spite of the existence of differences in some phenotypes, can provide important clues to the understanding of the pathogenesis of these disorders and are also very valuable for testing strategies for therapeutic approaches (Vainzof M, et al., 2008).

The mdx mouse model is a well-accepted animal model of human DMD. The mdx mouse carries a premature stop codon in exon 23 of the dystrophin gene and exhibits no detectable levels of dystrophin in muscle tissue. The progression of disease pathology in the dystrophic mdx mouse has been associated with constitutive activation of the MAP kinase, JNK1 (Kolodziejczyk et al. 2001), a ubiquitous signaling molecule. Once activated, JNK1 can phosphorylate the transcription factor NF-ATc1, leading to cytoplasmic accumulation and loss of NF-ATc1 function. Direct inhibition of JNK1 in dystrophic muscle, by overexpression of the JNK1 scaffolding protein JIP-1, was shown to reduce damage associated with typical disease progression (Kolodziejczyk et al. 2001). The present inventors have previously shown that the glucocorticoid, deflazacort, attenuates DMD pathology by circumventing and limiting the deleterious effects of JNK1 (St-Pierre et al. 2004). Deflazacort did not directly inhibit JNK1, rather the beneficial effects of this compound appear to originate from increasing the activity of the calcineurin phosphatase. Once activated, calcineurin then dephosphorylates NF-ATc1, restoring NF-ATc1 nuclear localization and transcriptional function (St-Pierre et al. 2004). Other groups have now demonstrated that increased calcineurin activity alleviates dystrophic muscle pathology (Chakkalakal et al. 2004; Chakkalakal et al. 2006; Stupka et al. 2006; Stupka et al. 2008).

A general interpretation of these studies is that calcineurin activation enhances myofiber integrity by increasing the expression of the dystrophin homologue utrophin, which itself provides an effective substitute for dystrophin in animal models of DMD. (St-Pierre et al. 2004; Chakkalakal et al. 2004; Chakkalakal et al. 2006). In agreement with this, enhanced utrophin expression has been shown to be an effective therapeutic intervention in a variety of dystrophy models (reviewed in Chakkalakal et al. 2005).

Currently, there are no cures for muscular dystrophy. Despite diligent research efforts to identify new therapeutic agents and new interventions for the treatment and management of MD, including of DMD, there has been limited success to date. Current treatments for DMD consist primarily of supportive care, including physical rehabilitation with braces, wheelchairs and ventilators, which can temporarily slow progression of disease and are essential in preventing complications and improving quality of life.

Corticosteroids (e.g., prednisone, prednisolone and deflazacort) are the only drugs that have been extensively studied as a pharmacologic therapy for DMD. However, controversies exist over their use because of the associated adverse effects, which include excessive weight gain, behavioral abnormalities, redistribution of body fat to the face and abdomen and away from the limbs, excessive hair growth, increased bone thinning and gastric ulceration, among others.

Prednisone is a synthetic corticosteroid drug that is usually taken orally, but can also be delivered by intramuscular injection. It is the corticosteroid most commonly prescribed for the treatment of DMD in North America. As with other steroid drugs, it is used to treat a number of different diseases and conditions. Prednisone is a prodrug that is converted by the liver into prednisolone, which is the active steroid. Prednisone can be effective in delaying the onset of symptoms of DMD, although the mechanism for the delay of symptoms is unknown.

Gene therapy offers future hope in the treatment of inherited single gene disorders, such as DMD, through targeting genetic defects and helping restore the defective protein. Indeed, it is widely believed that in the future, gene therapy could provide the cure for disorders such as DMD because it targets the disorder directly, whereas most other forms of treatment target only the symptoms of disease. However, at the present time, such therapy remains a distant reality and there is an immediate need for new and improved treatments.

It is, therefore, desirable to provide new compositions and methods for treating muscle diseases and conditions, including but not limited to, muscular dystrophy.

SUMMARY OF ASPECTS AND EXEMPLARY EMBODIMENTS

In one aspect, there is provided, a therapeutic agent for treating or preventing a muscle disease or condition characterized by impaired insulin-dependent signaling in muscle tissue. In another aspect, there is provided, a composition for treating or preventing a muscle disease or condition characterized by impaired insulin-dependent signaling in muscle tissue. The therapeutic agent is an activator of the insulin signaling pathway.

In some embodiments, the therapeutic agent exerts effects downstream of IRS-1 in the pathway. For example, the therapeutic agent may exert effects either directly or indirectly on effector molecules downstream of IRS-1 in the insulin signaling pathway. The therapeutic agent may, for example, exert one or more of the following effects: inhibition of JNK1; activation of AMPK; activation of AKT; or inhibition of GSK3β.

In some embodiments, the therapeutic agent inhibits JNK1. In some embodiments, the therapeutic agent activates AMPK. In some embodiments, the therapeutic agent activates AKT. In some embodiments, the therapeutic agent inhibits GSK3β.

In some embodiments, the therapeutic agent is selected from the group consisting of biguanides, AMPK activators, and analogues and derivatives thereof. In some embodiments, the therapeutic agent is a biguanide, such as, metformin or an analogue or derivative thereof. In some embodiments, the therapeutic agent is metformin.

In some embodiments, the therapeutic agent is a biguanide derivative. The biguanide derivative may, for example, be a prodrug. In some embodiments, the prodrug is a compound of Formula II:

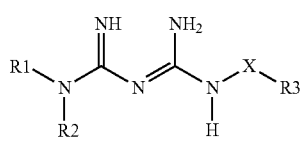

Formula II wherein:
R1 and R2 are independently selected from the group consisting of H, alkyl, alkoxy, haloalkyl, hydroxyalkyl, cyanoalkyl, alkenyl, alkynyl, cycloalkyl, cycloalkenyl, heterocycloalkyl, heterocycloalkenyl, aryl, heteroaryl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl, C(O)-alkyl, C(O)-alkyl, C(O)-cycloalkyl, C(O)-cycloalkyl, C(O)-heterocycloalkyl, S(O)2-heterocycloalkyl, alkylene-O-aryl, alkylene-O-heteroaryl, alkylene-O-alkylene-aryl, alkylene-O-alkylene-heteroaryl, C(O)alkyl, OC(O)alkyl, C(O)Oalkyl, C(O)N(H)alkyl, C(O)N(alkyl)alkyl, S(O)2N(H)alkyl or S(O)2N(alkyl)alkyl;

R3 is selected from the group consisting of C1- to C8-lower alkyl, C1- to C8-lower alkoxy, C1- to C8-lower alkyl-ester, cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;

X is selected from the group consisting of lower-alkyl, O, C(O), C(O)2, C(O)N, S, S(O), S(O)2 and P(O)3;

and/or a pharmaceutically-acceptable salt, hydrate, solvate, isoform, tautomer, optical isomer, or combination thereof.

In some embodiments, the compound of Formula II is a compound of Formula IIA, IIB, IIC, IID or IIE:

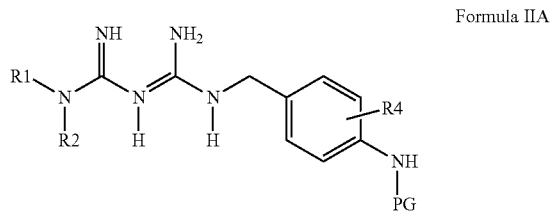

Formula IIA

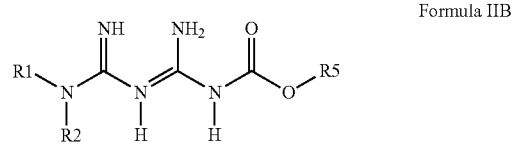

Formula IIB

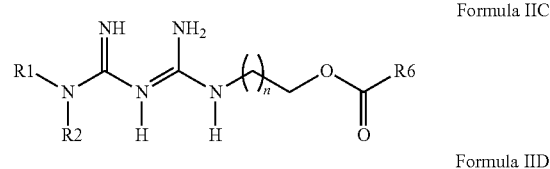

Formula IIC

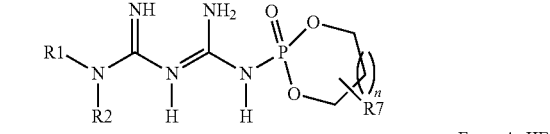

Formula IID

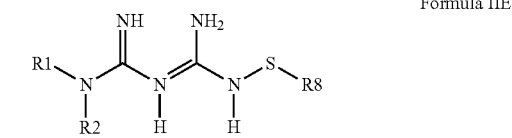

Formula IIE

Wherein:
R1 and R2 are independently selected from the group consisting of H, alkyl, alkoxy, haloalkyl, hydroxyalkyl, cyanoalkyl, alkenyl, alkynyl, cycloalkyl, cycloalkenyl, heterocycloalkyl, heterocycloalkenyl, aryl, heteroaryl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl, C(O)-alkyl, C(OO)-alkyl, C(O)-cycloalkyl, C(OO)-cycloalkyl, C(O)- heterocycloalkyl, S(O)2-heterocycloalkyl, alkylene-O-aryl, alkylene-O-heteroaryl, alkylene-O-alkylene-aryl, alkylene-O-alkylene-heteroaryl, C(O)alkyl, OC(O)alkyl, C(O)Oalkyl, C(O)N(H)alkyl, C(O)N(alkyl)alkyl, S(O)2N(H)alkyl or S(O)2N(alkyl)alkyl;

R4 is selected from the group consisting of H, hydroxy, halogen, cyano, nitro, carboxylic ester, carboxylic acid, carboxylic amide, C1- to C8-lower alkyl, C1- to C8-lower alkoxy, C1- to C8-lower alkyl-ester, cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;

R5 to R8 are independently selected from the group consisting of C1- to C8-lower alkyl, C1- to C8-lower alkoxy, C1- to C8-lower alkyl-ester, halo-alkyl-ester cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl; and n is selected from 1 to 4 and m from 0 to 2.

In some embodiments, R1 and R2 are independently selected from the group consisting of alkyl, cycloalkyl and heterocycloalkyl. In some embodiments, R5, R6, R7 and R8 are independently selected from the group consisting of C1- to C8-lower alkyl, cycloalkyl, heterocycloalkyl, aryl and heteroaryl; and/or a pharmaceutically-acceptable salt, hydrate, solvate, isoform, tautomer, optical isomer, or combination thereof.

In some embodiments, the therapeutic agent is N1,N1-Dimethyl-S-cyclohexyl-N4-thiohydroxylbiguanidine. In some embodiments, the therapeutic agent is N1,N1-Dimethyl-S-phenyl-N4-thiohydroxylbiguanidine. In some embodiments, the therapeutic agent is tert-Butyl 4-[(3-(N,N-Dimethylcarbamimidoyl)guanidino)methyl]phenyl carbamate. In some embodiments, the therapeutic agent is 4-{[3-(N,N-Dimethylcarbamimidoyl)guanidino]methyl}phenyl-octanoate. In some embodiments, the therapeutic agent is 4-{[3-(N,N-Dimethylcarbamimidoyl)guanidino]methyl}phenyl-diethylcarbamate. In some embodiments, the therapeutic agent is 4-[(3-(N,N-Dimethylcarbamimidoyl)guanidino)methyl]-3-hydroxyphenyl-pivalate. In some embodiments, the therapeutic agent is 3-[3-(N,N-Dimethylcarbamimidoyl)guanidino]propyl-acetate. In some embodiments, the therapeutic agent is [(N',N'-Dimethylguanidino)iminomethyl]carbamic acid benzyl-ester. In some embodiments, the therapeutic agent is [(N',N'-Dimethylguanidino)iminomethyl]carbamic acid 2,2,2-trichloroethyl-ester. In some embodiments, the therapeutic agent is [(N1,N1-Dimethylcarbamimidoyl)guanidino]-4-phenyl-1,3,2-dioxaphosphoramidate. In some embodiments, the therapeutic agent is a pharmaceutically-acceptable salt, hydrate, solvate, isoform, tautomer, optical isomer, or combination thereof, of any of the above compounds.

In some embodiments, the compositions disclosed herein comprise at least one pharmaceutically acceptable carrier and/or excipient.

In some embodiments, the disease or condition characterized by impaired insulin-dependent signaling in muscle tissue is a muscular dystrophy. In some embodiments, the muscular dystrophy is Duchenne muscular dystrophy, Becker muscular dystrophy, a limb-girdle muscular dystrophy, or a related dystrophy. In some embodiments, the muscular dystrophy is Duchenne muscular dystrophy.

In some embodiments, the compositions disclosed herein further comprise a corticosteroid, for example, prednisone, prednisolone, deflazacort, or a combination thereof. In some embodiments, corticosteroid is prednisone. In some embodiments, the corticosteroid is prednisolone. In some embodiments, the corticosteroid is deflazacort.

In some embodiments, a composition as disclosed herein comprises metformin and a corticosteroid. In some embodiments, a composition as disclosed herein comprises metformin and a prednisone. In some embodiments, a composition as disclosed herein comprises metformin and a prednisolone. In some embodiments, a composition as disclosed herein comprises metformin and a deflazacort.

In another aspect, there is provided a biguanide derivative selected from the group consisting of:

N1,N1-Dimethyl-S-cyclohexyl-N4-thiohydroxylbiguanidine;

N1,N1-Dimethyl-S-phenyl-N4-thiohydroxylbiguanidine;

tert-Butyl 4-[(3-(N,N-Dimethylcarbamimidoyl)guanidino)methyl]phenyl-carbamate;

4-{[3-(N,N-Dimethylcarbamimidoyl)guanidino]methyl}phenyl-octanoate;

4-{[3-(N,N-Dimethylcarbamimidoyl)guanidino]methyl}phenyl-diethylcarbamate;

4-[(3-(N,N-Dimethylcarbamimidoyl)guanidino)methyl]-3-hydroxyphenyl-pivalate;

3-[3-(N,N-Dimethylcarbamimidoyl)guanidino]propyl-acetate;

[(N',N'-Dimethylguanidino)iminomethyl]carbamic acid benzyl-ester;

[(N',N'-Dimethylguanidino)iminomethyl]carbamic acid 2,2,2-trichloroethyl-ester;

[(N1,N1-Dimethylcarbamimidoyl)guanidino]-4-phenyl-1,3,2-dioxaphosphoramidate; and/or a pharmaceutically-acceptable salt, hydrate, solvate, isoform, tautomer, optical isomer, or combination thereof.

In another aspect, there is provided a method of treating or preventing a muscle disease or condition characterized by impaired insulin-dependent signaling in muscle tissue, comprising administering to a subject in need thereof a therapeutically effective amount of a composition comprising a therapeutic agent as defined herein. A subject in need thereof may be a subject that has, is suspected of having, or is at risk of developing a muscle disease or condition characterized by impaired insulin-dependent signaling.

In some embodiments, the therapeutic agent is metformin or an analogue or derivative thereof.

In some embodiments, the therapeutic agent is metformin.

In some embodiments, the method further comprises administering a corticosteroid to the subject. In some embodiments, the corticosteroid is prednisone, prednisolone, deflazacort, dexamethasone or a combination thereof. In some embodiments, the corticosteroid is prednisone. In some embodiments, the corticosteroid is prednisolone. In some embodiments, the corticosteroid is deflazacort. In some embodiments, the corticosteroid is dexamethasone. The corticosteroid may be administered to the subject together with or separately from the therapeutic agent. For instance, the corticosteroid may be administered to the subject prior to, concurrently with, or subsequent to the therapeutic agent. In some embodiments, the corticosteroid is administered to the subject prior to the therapeutic agent. In some embodiments, corticosteroid is administered to the subject concurrently with the therapeutic agent. In some embodiments, the corticosteroid is administered to the subject subsequent to the therapeutic agent.

The therapeutic agent may be administered by any suitable route of administration, for example, local or systemic routes of administration. In some embodiments, the therapeutic agent is administered orally or parenterally. In some embodiments, the therapeutic agent is administered orally. In some embodiments, the therapeutic agent is administered parenterally. In some embodiments, the parenteral administration is intramuscular, subcutaneous, intravenous, or intraarterial. In some embodiments, the parenteral administration is intramuscular. In some embodiments, the parenteral administration is intravenous. In some embodiments, the parenteral administration is intraarterial.

In another aspect, there is provided a method of treating Duchenne muscular dystrophy comprising administering to a patient a therapeutically effective amount of metformin. In some embodiments, the method further comprises administration of a corticosteroid. In some embodiments, the metformin and the corticosteroid are administered together. In some embodiments, the metformin and the corticosteroid are administered separately.

In another aspect, there is provided a kit or commercial package for the treatment of muscular dystrophy comprising metformin and instructions for use in the treatment of muscular dystrophy.

In another aspect, there is provided a kit or commercial package for the treatment of muscular dystrophy comprising, metformin and a corticosteroid, together with instructions for their administration in a combination therapy.

In another aspect, there is provided a use of a composition as described herein for the treatment or prevention of a muscle disease or condition characterized by impaired insulin dependent signaling.

In another aspect, there is provided a use of the composition of a composition as described herein for the manufacture of a medicament for the treatment or prevention of a muscle disease or condition characterized by impaired insulin dependent signaling.

In another aspect, there is provided a composition as described herein for the treatment or prevention of a muscle disease or condition characterized by impaired insulin dependent signaling.

In another aspect, there is provided metformin or an analogue or derivative thereof for the treatment or prevention of a muscle disease or condition characterized by impaired insulin dependent signaling.

In another aspect, there is provided a combination of metformin or an analogue or derivative thereof and a corticosteroid for the treatment or prevention of a muscle disease or condition characterized by impaired insulin dependent signaling.

In another aspect, there is provided a method of determining whether a patient suffering from a muscle disease or condition would benefit from treatment with an activator of the insulin signaling pathway comprising: obtaining a muscle-derived biological sample from the subject; and testing the sample for impaired insulin dependent signaling, wherein the identification of impaired insulin dependent signaling is indicative that the patient would benefit from treatment with an activator of the insulin signaling pathway. In some embodiments, the method further comprises the step of administering an activator of the insulin signaling pathway to the patient. In some embodiments, the activator of the insulin signaling pathway is metformin or a derivative thereof.

Other aspects and features will become apparent to those ordinarily skilled in the art upon review of the following description of specific embodiments in conjunction with the accompanying figures.

BRIEF DESCRIPTION OF THE DRAWINGS

Embodiments will now be described, by way of example only, with reference to the attached Figures, wherein.

DETAILED DESCRIPTION

Figure 1:
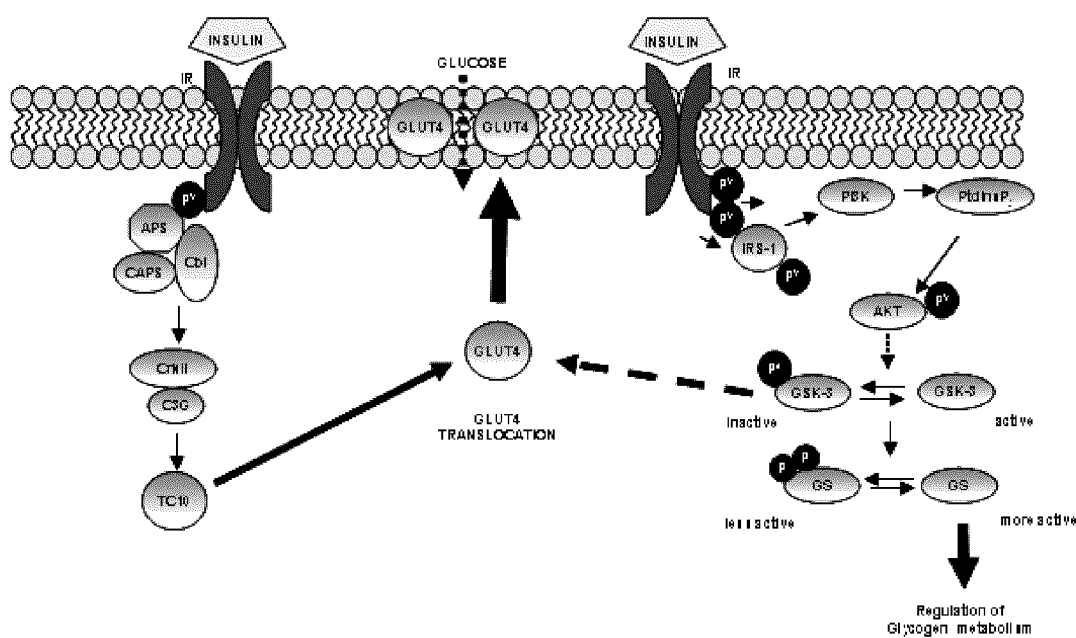
FIG. 1 is a Schematic Representation of the Insulin-Dependent Signaling Pathways. Insulin binds to its receptor (IR) leading to autophosphorylation, catalyzing the phosphorylation of insulin receptor substrates (IRS). Upon tyrosine phosphorylation, IRS activates phosphoinositide 3-kinase (PI3K), PIP2 and PIP. This, in turn, activates phosphatidylinositol3 (PtdInsP3), which subsequently activates AKT/PKB. Once active, AKT phosphorylates and thus inactivates glycogen synthase kinase 3 (GSK3). This results in the translocation of the glucose transporter (GLUT4) from cytoplasmic vesicles to the cell membrane. Glycogen synthase (GS) is a major substrate of GSK3 and catalyses the final step in glycogen synthesis. Phosphorylation of glycogen synthase by GSK3 inhibits glycogen synthesis; therefore the inactivation of GSK3 by AKT promotes glucose storage as glycogen. Additionally, autophosphorylation of the IR also results in activation of the Cpl-CAP-APS complex leading to formation of CrkII-C3G complex which stimulates TC10 activity. These pathways act to coordinate the regulation of vesicle trafficking, protein synthesis and gene expression, which results in the regulation of glucose, lipid and protein metabolism.

Generally, the present disclosure provides therapeutic agents, compositions and methods for treating muscle diseases or conditions characterized by metabolic disturbance in muscle tissue, in particular, impaired insulin-dependent signaling.

It is demonstrated herein that certain muscle diseases and conditions are characterized by metabolic disturbances in the muscle tissue itself. In particular, it is demonstrated that dystrophic muscle exhibits impaired insulin-dependent signaling, in essence, a form of insulin resistance. It is further demonstrated that treating the underlying defect in insulin signaling results in a significant improvement in disease pathology, at both the molecular and behavioral levels. Thus, diseases or conditions characterized by this metabolic disturbance may be alleviated by administering a therapeutic agent for correcting the underlying defect in insulin-dependent signaling. It is believed that these findings represent a significant scientific advance in the understanding of muscle disease, including muscular dystrophy, and also represent a much-needed therapeutic advance in this field.

Various non-limiting aspects and embodiments are described herein. A skilled person having regard to the present disclosure will appreciate that the scope of the invention is not limited to the exemplary aspects and embodiments disclosed herein.

The term "impaired insulin-dependent signaling" refers generally to a form of insulin resistance wherein cells become less sensitive to the effects of insulin. More particularly, as used herein, "impaired insulin-dependent signaling" refers to an impairment that results in elevated phosphorylation of the IRS-1 at serine 307 leading to inhibition in insulin signaling. The term "defective" insulin signaling is also used herein.

In some embodiments, the muscle disease or condition characterized by impaired insulin-dependent signaling is one or more of a muscle degenerative disease, a myopathy, or a disease or condition characterized by muscle wasting or atrophy. A skilled person will appreciate that other muscle diseases and conditions besides those listed above may be tested and found to be characterized by impaired insulin-dependent signaling. Such muscle diseases and conditions are considered within the scope of the present disclosure.

In some embodiments, the muscle disease or condition characterized by impaired insulin-dependent signaling is a muscle degenerative disease, including but not limited to a muscular dystrophy. Muscular dystrophies include, but are not limited to, Duchenne muscular dystrophy (DMD), Becker muscular dystrophy, limb-girdle muscular dystrophies, myotonic dystrophy (also known as Steinert's disease), facioscapulohumeral muscular dystrophy, congenital muscular dystrophies, oculopharyngeal muscular dystrophy, distal muscular dystrophies and Emery-Dreifuss muscular dystrophy. See, e.g., Hoffman et al., N. Engl. J. Med., 318.1363-1368 (1988); Bonnemann, C. G. et al., Curr. Opin. Ped., 8: 569-582 (1996); Worton, R., Science, 270: 755-756 (1995); Funakoshi, M. et al., Neuromuscul. Disord., 9 (2): 108-114 (1999); Lim, L. E. and Campbell, K. P., Cure. Opin. Neurol., 11 (5): 443-452 (1998); Voit, T., Brain Dev., 20 (2): 65-74 (1998); Brown, R. H., Annu. Rev. Med., 48: 457-466 (1997); Fisher, J. and Upadhyaya, M., Neuromuscul. Disord., 7 (1): 55-62 (1997).

In some embodiments, the muscular dystrophy is Duchenne muscular dystrophy, Becker muscular dystrophy, a Limb-Girdle muscular dystrophy, myotonic dystrophy or a related dystrophy characterized by impaired insulin-dependent signaling. In some embodiments, the muscular dystrophy originates from disruptions in the dystrophin-dystroglycan complex. In some embodiments, the muscular dystrophy is Duchenne muscular dystrophy (DMD). In some embodiments, the muscular dystrophy is Becker muscular dystrophy (BMD). In other embodiments, the muscular dystrophy is a Limb-Girdle muscular dystrophy. In other embodiments, the muscular dystrophy is myotonic dystrophy. In some embodiments, the muscular dystrophy is a congenital muscular dystrophy characterized by impaired insulin dependent signaling.

In some embodiments, the muscle disease or condition characterized by impaired insulin-dependent signaling is a disease or condition characterized by muscle wasting or atrophy, for example, a disuse atrophy, for example, sarcopenia or intensive care atrophy.

In some embodiments, the disease or condition is a myopathy. In some embodiments, the disease or condition is a critical illness myopathy, which may, for example, be brought about from bone marrow transplant, sepsis, multi-organ failure, or prolonged mechanical ventilation. This is referred to in the literature as CINMA or critical illness neuromuscular abnormalities and it affects approximately 50% of all ICU patients.

In accordance with the present disclosure, there are contemplated therapeutic agents, compositions and methods for treating and/or preventing a disease or condition characterized by impaired insulin dependent signaling. The therapeutic agent targets the underlying signaling defect.

A "therapeutic agent" is a molecule or group of molecules for eliciting a desired therapeutic effect and may include, for example, organic and inorganic small molecules, peptides and polypeptides, polymers, fusion proteins, polynucleotides, oligonucleotides, antibodies or antibody fragments, macromolecules, encapsulated molecules, among others. In accordance with the present disclosure, there are described therapeutic agents for treating or preventing a muscle condition or disease characterized by impaired insulin-dependent signaling.

In some embodiments, the therapeutic agent is an "activator of the insulin signaling pathway" that preferably exerts its effects, at least in part, downstream of IRS-1. When referring to activation of a signaling pathway, "activation" may occur directly (e.g. via activation, stimulation or up-regulation of an activating component of a signaling pathway) or may occur indirectly (e.g. via inhibition or down-regulation of an inhibitory component of the pathway). The converse is also true where "inhibition" may occur directly or indirectly.

Activators of the insulin signaling pathway may act at a genetic level, for example, to upregulate or downregulate the expression of a gene of interest, or they may act at the protein level, for example, to increase or decrease the activity of a polypeptide of interest. Exemplary activators of the insulin signaling pathway may include activators or inhibitors of one or more downstream effector molecules in the insulin signaling pathway (e.g. IRS-1/AKT/GSK3). Activators of the insulin signaling pathway may also target molecules that affect the insulin signaling pathway, such as AMPK and JNK1. For example, in some embodiments, the therapeutic agent may be an AKT activator, AMPK activator, GSK3β inhibitor, or JNK1 inhibitor, among others.

In some embodiments, the activator of the insulin signaling pathway is an AMPK activator. Exemplary AMPK activators include A-769662 9 (a non-nucleoside compound from the thienopyridone family), GW-501516 (which activates PPAR-gamma and AMPK), and AICAR (aminoimidazole carboxamide ribonucleotide). As a combination therapy, GW-501516 has been shown to act synergistically with AICAR. The thiazolidinedione (activators of PPAR-gamma) class of drugs may also be considered AMPK activators.

In some embodiments, the activator of the insulin signaling pathway is a JNK inhibitor. Exemplary JNK inhibitors include, for example, SP600125 and BI-78D3. BI-78D3 was recently demonstrated to alleviate insulin resistance in a murine model of type-II diabetes (Stebbins et al, 2008) and it therefore predicted to have beneficial effects in accordance with the present disclosure.

In some embodiments, the therapeutic agent which activates the insulin signaling pathway is an organic or inorganic small molecule. "Small molecule", as used herein, generally means a low molecular weight (e.g. less than 1000 Da, often less than 800 Da, often than 500 Da) organic compound. In some cases, a subunit of a polymer, or a small peptide, can be considered within the definition of a small molecule.

In some embodiments, the therapeutic agent is a biguanide or an analogue or derivative thereof. Biguanides include, for example, metformin, phenformin, buformin, and proguanil. The biguanide or biguanide derivative selected should be capable of treating impaired insulin-dependent signaling in a muscle condition or disease characterized thereby, for example, by activating the insulin signaling pathway whether directly or indirectly.

In some embodiments, the biguanide is metformin (N,N-dimethylimidodicarbonimidicdiamide) or an analogue or derivative thereof.

Metformin has the following structural formula (Formula I):

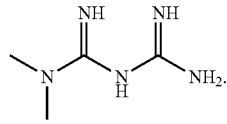

Metformin has been widely prescribed for over 50 years to treat insulin resistance in diabetic patients. Thus, in one aspect, the present disclosure provides for the re-purposing of a safe and well-established anti-diabetic drug to provide a new and effective treatment for a muscle disease or condition characterized by impaired insulin-dependent signaling.

Metformin has a low toxicity profile. The most serious complication associated with metformin is lactic acidosis, which has an incidence of about 0.03 cases per 1000 patients years of treatment and a mortality risk of about 0.015 per 1000 patient-years. Most cases occur in patients with impaired renal function (e.g. serum creatinine level>130 µmol/L or >1.5 g/L). Other major contraindications include congestive heart failure, hypoxic states and advanced liver disease. Serious adverse events with metformin are predictable rather than spontaneous and are potentially preventable if the prescribing guidelines are respected. Gastrointestinal adverse effects, notably diarrhea, occur in less than 20% of patients and remit when the dosage is reduced. The life-threatening risks associated with metformin are rare and could mostly be avoided by strict adherence to the prescribing guidelines. Given the 5 decades of clinical experience with metformin, its antihyperglycaemic efficacy, and benefits against Syndrome X, metformin offers a very favorable risk-benefit assessment when compared with the chronic morbidity and premature mortality among patients with type 2 diabetes mellitus. Metformin is commercially available from a variety of sources.

In some embodiments, the therapeutic agent is a derivative of a biguanide. As used herein, "derivative" includes, but is not limited to, prodrug forms, pegylated forms, etc.

The prodrug approach is a chemical approach using reversible derivatives, which can be useful in optimizing the clinical application of a therapeutic agent. Prodrugs have been designed and developed, for example, to overcome pharmaceutical and pharmacokinetic barriers in clinical drug application, such as low oral drug absorption, lack of site specificity, chemical instability, toxicity, and poor patient acceptance (Han, 2000). As used herein, "prodrug" generally refers to a compound that, upon in vivo administration, is metabolized or otherwise converted to the biologically, pharmaceutically or therapeutically active form of the compound. To produce a prodrug, generally the pharmaceutically active compound is modified such that the active compound is regenerated, enzymatically or nonenzymatically, to exert a therapeutic effect. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady 1985, Stella et al. 1985, Banerjee et al. 1985).

In some embodiments, the therapeutic agent is a prodrug of a biguanide.

In some embodiments, the biguanide prodrug is a compound of Formula II:

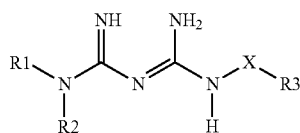

Formula II wherein:

R1 and R2 are independently selected from the group consisting of H, alkyl, alkoxy, haloalkyl, hydroxyalkyl, cyanoalkyl, alkenyl, alkynyl, cycloalkyl, cycloalkenyl, heterocycloalkyl, heterocycloalkenyl, aryl, heteroaryl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl, C(O)-alkyl, C(OO)-alkyl, C(O)-cycloalkyl, C(OO)-cycloalkyl, C(O)-heterocycloalkyl, S(O)$_2$-heterocycloalkyl, alkylene-O-aryl, alkylene-O-heteroaryl, alkylene-O-alkylene-aryl, alkylene-O-alkylene-heteroaryl, C(O)alkyl, OC(O)alkyl, C(O)Oalkyl, C(O)N(H)alkyl, C(O)N(alkyl)alkyl, S(O)$_2$N(H)alkyl or S(O)$_2$N(alkyl)alkyl;

R3 is selected from the group consisting of C$_1$- to C$_8$-lower alkyl, C$_1$- to C$_8$-lower alkoxy, C$_1$- to C$_8$-lower alkyl-ester, cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;

X is selected from the group consisting of lower-alkyl, O, C(O), C(O)$_2$, C(O)N, S, S(O), S(O)$_2$ and P(O)$_3$;

and/or a pharmaceutically-acceptable salt, hydrate, solvate, isoform, tautomer, optical isomer, or combination thereof;

In some embodiments, the compound of Formula II comprises a compound of any one of Formula IIA, IIB, IIC, IID or IIE:

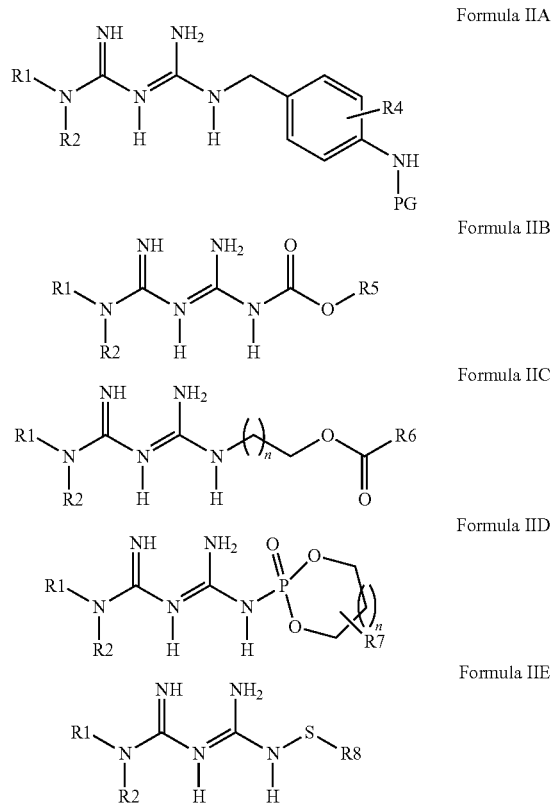

Wherein:

R1 and R2 are independently selected from the group consisting of H, alkyl, alkoxy, haloalkyl, hydroxyalkyl, cyanoalkyl, alkenyl, alkynyl, cycloalkyl, cycloalkenyl, heterocycloalkyl, heterocycloalkenyl, aryl, heteroaryl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl, C(O)-alkyl, C(O)-alkyl, C(O)-cycloalkyl, C(O)-cycloalkyl, C(O)-heterocycloalkyl, S(O)$_2$-heterocycloalkyl, alkylene-O-aryl, alkylene-O-heteroaryl, alkylene-O-alkylene-aryl, alkylene-O-alkylene-heteroaryl, C(O)alkyl, OC(O)alkyl, C(O)Oalkyl, C(O)N(H)alkyl, C(O)N(alkyl)alkyl, S(O)$_2$N(H)alkyl or S(O)$_2$N(alkyl)alkyl;

R4 is selected from the group consisting of H, hydroxy, halogen, cyano, nitro, carboxylic ester, carboxylic acid, carboxylic amide, C$_1$- to C$_8$-lower alkyl, C$_1$- to C$_8$-lower alkoxy, C$_1$- to C$_8$-lower alkyl-ester, cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;

R5 to R8 are independently selected from the group consisting of C$_1$- to C$_8$-lower alkyl, C$_1$- to C$_8$-lower alkoxy, C$_1$- to C$_8$-lower alkyl-ester, halo-alkyl-ester cycloalkyl, heterocycloalkyl, bicycloalkyl, heterobicycloalkyl, aryl, heteroaryl, optionally-substituted aryl, optionally-substituted hetero-aryl; hydroxyalkyl, hydroxycycloalkyl, hydroxy-heterocycloalkyl, cyanoalkyl, alkenyl, alkynyl, cycloalkyl, cycloalkenyl, heterocycloalkyl, heterocycloalkenyl, alkylaryl, alkylheteroaryl, alkylene-O-alkyl, alkylene-O-cycloalkyl, alkylene-O-heterocycloalkyl, alkylene-O-alkylene-cycloalkyl, alkylene-O-alkylene-heterocycloalkyl;

In some embodiments, n is selected from 1 to 4 and m from 0 to 2;

In some embodiments of the compounds of Formula II, R1 and R2 are independently selected from the group consisting of alkyl, cycloalkyl and heterocycloalkyl;

In yet other embodiments of the compound of Formula II, R5, R6, R7 and R8 are independently selected from the group consisting of $C_1$- to $C_8$-lower alkyl, cycloalkyl, heterocycloalkyl, aryl and heteroaryl; and/or a pharmaceutically-acceptable salt, hydrate, solvate, isoform, tautomer, optical isomer, or combination thereof;

Some exemplary prodrugs include the following compounds, their pharmaceutically acceptable salts, hydrates, solvates, optical isomers, and combinations thereof:

$N^1,N^1$-Dimethyl-S-cyclohexyl-$N^4$-thiohydroxylbiguanidine;
$N^1,N^1$-Dimethyl-S-phenyl-$N^4$-thiohydroxylbiguanidine;
tert-Butyl 4-[(3-(N,N-Dimethylcarbamimidoyl)guanidino)methyl]phenyl-carbamate;
4-{[3-(N,N-Dimethylcarbamimidoyl)guanidino]methyl}phenyl-octanoate;
4-{[3-(N,N-Dimethylcarbamimidoyl)guanidino]methyl}phenyl-diethylcarbamate;
4-[(3-(N,N-Dimethylcarbamimidoyl)guanidino)methyl]-3-hydroxyphenyl-pivalate;
3-[3-(N,N-Dimethylcarbamimidoyl)guanidino]propyl-acetate;
[(N',N'-Dimethylguanidino)iminomethyl]carbamic acid benzyl-ester;
[(N',N'-Dimethylguanidino)iminomethyl]carbamic acid 2,2,2-Trichloroethyl-ster;
[($N^1,N^1$-Dimethylcarbamimidoyl)guanidino]-4-phenyl-1,3,2-dioxaphosphoramidate;
and/or a pharmaceutically-acceptable salt, hydrate, solvate, isoform, tautomer, optical isomer, or combination thereof.

Acid addition salts of the compounds of Formula II are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula II for laboratory use, or for subsequent conversion to a pharmaceutically acceptable acid addition salt. Also included within the scope are base addition salts (such as sodium, potassium and ammonium salts), solvates and hydrates of compounds disclosed herein. The conversion of a given compound salt to a desired compound salt is achieved by applying standard techniques, well known to one skilled in the art.

The conversion of a given compound salt to a desired compound salt is achieved by applying standard techniques, well known to one skilled in the art.

Several methods for preparing compounds of Formula II are illustrated in the following Schemes and in the Examples section. Starting materials and the requisite intermediates are in some cases commercially available or can be prepared according to literature procedures (Huttunen, 2009, Huttunen 2008) or as illustrated herein.

Certain prodrug compounds of Formula IIA, wherein R1 and R2 are independently selected from alkyl group, and X—R3 is either substituted protected p-amino or p-hydroxybenzylic groups, can be prepared in accordance with Scheme 1.

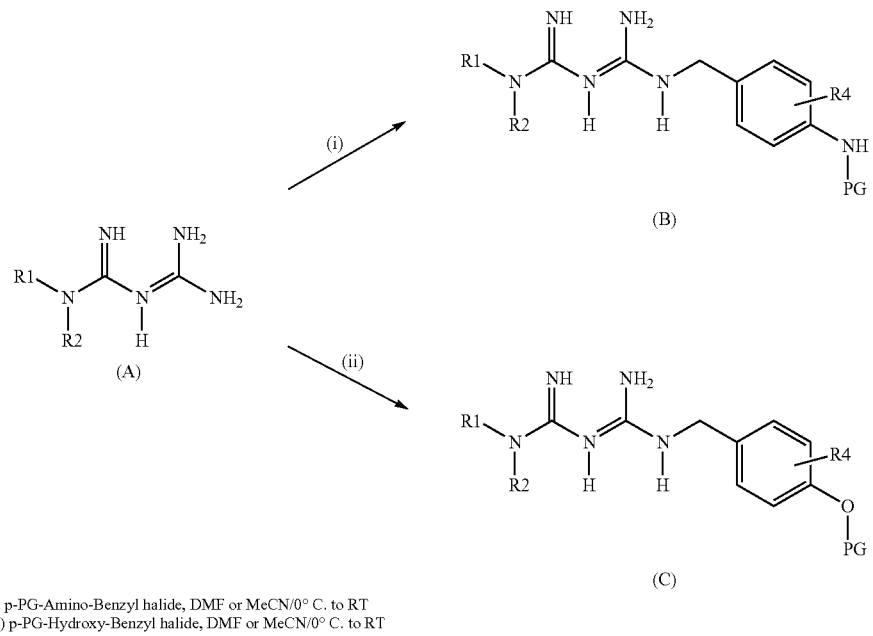

(i) p-PG-Amino-Benzyl halide, DMF or MeCN/0° C. to RT
(ii) p-PG-Hydroxy-Benzyl halide, DMF or MeCN/0° C. to RT Condensation of N,N-dialkyl-metformin A with an appropriately substituted benzyl-halide (e.g. tert-butyl 4-(Chloro or Bromomethyl)phenylcarbamate and 4-(Chloro or Bromomethyl)phenyl alcanoate) in polar solvent such as DMF or MeCN at 0° C. under argon led, after purification by flash chromatography to the targeted prodrug compounds B and C respectively.

In yet another embodiment, there is provided a method of preparing a compound of Formula IIB, wherein R1 and R2 are independently selected from alkyl group, and X—R3 is a carbamic ester group, can be generally prepared in accordance with Scheme 2.

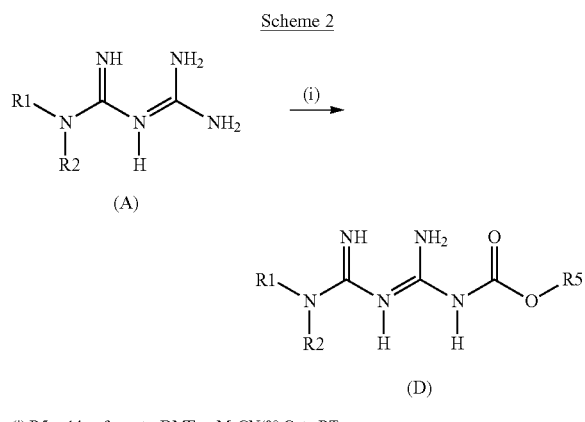

(i) R5 - chloroformate, DMF or MeCN/0° C. to RT

Condensation of N,N-dialkyl-metformin derivative A with an appropriate chloroformate (e.g. Benzyl chloroformate and 2,2,2-Trichloroethyl chloroformate) in a polar solvent, such as MeCN at 0° C. under argon led, after purification by flash chromatography to the targeted prodrug compounds D.

In yet a further aspect, the biguanide prodrug compounds, described by Formula IIC, wherein R1 and R2 are independently selected from alkyl group, and X—R3 is an alkyl-ester, can be generally prepared in accordance with Scheme 3.

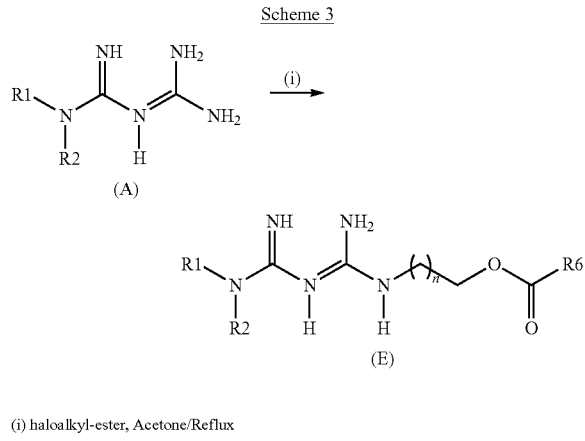

(i) haloalkyl-ester, Acetone/Reflux

Condensation of an appropriate haloalkyl-ester (e.g. 3-chloropropyl acetate) with N,N-dialkyl-metformin derivative A in anhydrous acetone under reflux led, after purification by flash chromatography, to the targeted biguanide prodrug compounds E.

In yet another aspect, certain biguanide prodrug compounds of Formula IID, wherein R1 and R2 are independently selected from alkyl group, and X—R3 is a substituted cyclic phosphate, can be prepared in accordance with Scheme 4.

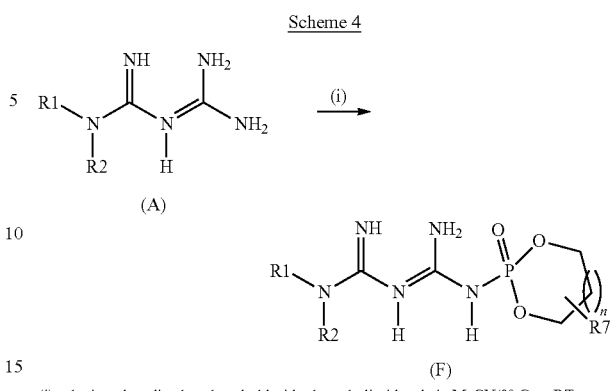

(i) substituted cyclic phosphoryl-chloride, 1-methylimidazole in MeCN/0° C. to RT Condensation of N,N-dialkyl-metformin derivative A with an appropriate substituted cyclic phosphoryl chloride (e.g. 2-Chloro-4-phenyl-[1,3,2]dioxa-phosphinane 2-oxide) and 1-methylimidazole in MeCN at 0° C. under argon to provide, after stirring overnight at room temperature and purification by flash chromatography, biguanide prodrug cyclic phosphates F.

In yet another aspect, biguanide prodrug compounds of Formula IE, wherein R1 and R2 are independently selected from alkyl group, X is Sulfur and —R3 is alkyl, cycloalkyl, heterocycloalkyl, aryl, heteroaryl, can generally be prepared in accordance with Scheme 5.

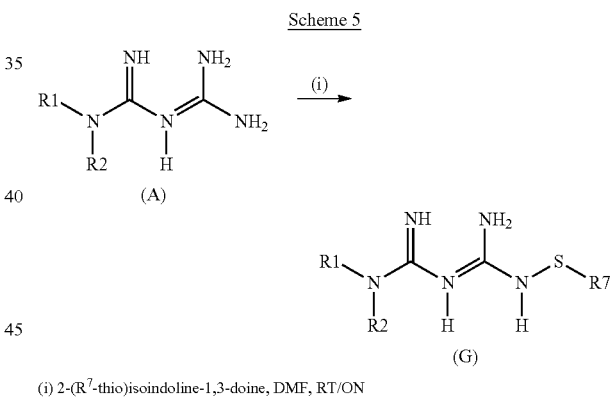

(i) 2-(R7-thio)isoindoline-1,3-doine, DMF, RT/ON

Condensation of N,N-dialkyl-metformin derivative A with an appropriate substituted 2-(thio)-isoindoline-1,3-dione derivative in anhydrous DMF under argon to provide, after stirring 24 hours at room temperature and purification by flash chromatography, thioxy-biguanide prodrug compounds G;

In some embodiments, the compound of Formula II is pharmaceutically-acceptable salt, optical isomer, or combination thereof.

In some embodiments, the pharmaceutically-acceptable salt comprises an acid addition salt or a basic addition salt.

In some embodiments, the prodrug compounds may have one or more asymmetric centres and it is intended that any optical isomers, as separated, pure or partially purified optical isomers or racemic mixtures thereof are included within the scope of the present application.

In some embodiments, some of the compounds disclosed herein may exist in different tautomeric forms and it is intended that any tautomeric forms which the compounds are able to form are included within the scope of the present application.

In some embodiments, the acid addition salt is formed from hydrochloric acid, hydrobromic acid, sulfuric acid, phosphoric acid, acid metal salt, monocarboxylic acids, dicarboxylic acids, or tricarboxylic acids.

Unless specified otherwise, the chemical nomenclature used herein generally follows the examples and rules stated in *Nomenclature of Organic Chemistry*, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program, e.g. ACD/ChemSketch, Version 5.09/September 2001, Advanced Chemistry Development, Inc., Toronto, Canada.

The compounds disclosed herein may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present disclosure.

Generally, reference to a certain element such as hydrogen or H is meant to, if appropriate, include all isotopes of that element.

The following terms are meant to encompass unsubstituted and/or substituted.

The term "alkyl" as used herein means a straight- or branched-chain hydrocarbon radical; in one aspect, having from one to eight carbon atoms, and includes, for example, and without being limited thereto, methyl, ethyl, propyl, isopropyl, t-butyl and the like. As noted above, "alkyl" encompasses substituted alkyl. Substituted alkyl includes, for example, and without being limited thereto, haloalkyl, hydroxyalkyl, cyanoalkyl, and the like. This is applied to any of the groups mentioned herein. Groups such as "alkenyl", "alkynyl", "aryl", etc. encompass substituted "alkenyl", "alkynyl", "aryl", etc.

The term "alkenyl" as used herein means a straight- or branched-chain alkenyl radical; in one aspect, having from two to eight carbon atoms, and includes, for example, and without being limited thereto, ethenyl, 1-propenyl, 1-butenyl and the like. The term "alkenyl" encompass radicals having "cis" and "trans" orientations, or alternatively, "E" and "Z" orientations.

The term "alkynyl" as used herein means a straight- or branched-chain alkynyl radical; in one aspect, having from two to eight carbon atoms, and includes, for example, and without being limited thereto, 1-propynyl (propargyl), 1-butynyl and the like.

The term "cycloalkyl" as used herein means a carbocyclic system (which may be unsaturated) containing one or more rings wherein such rings may be attached together in a pendent manner or may be fused. In one aspect, the ring(s) may have from three to seven carbon atoms, and includes, for example, and without being limited thereto, cyclopropyl, cyclohexyl, cyclohexenyl and the like.

The term "heterocycloalkyl" as used herein means a heterocyclic system (which may be unsaturated) having at least one heteroatom selected from N, S and/or O and containing one or more rings wherein such rings may be attached together in a pendent manner or may be fused. In one aspect, the ring(s) may have a three- to seven-membered cyclic group and includes, for example, and without being limited thereto, piperidinyl, piperazinyl, pyrrolidinyl, tetrahydrofuranyl and the like.

The term "alkoxy" as used herein means a straight- or branched-chain alkoxy radical; in one aspect, having from one to eight carbon atoms and includes, for example, and without being limited thereto, methoxy, ethoxy, propyloxy, isopropyloxy, t-butoxy and the like.

The term "halo" as used herein means halogen and includes, for example, and without being limited thereto, fluoro, chloro, bromo, iodo and the like, in both radioactive and non-radioactive forms.

The term "alkylene" as used herein means a difunctional branched or unbranched saturated hydrocarbon radical; in one aspect, having one to eight carbon atoms, and includes, for example, and without being limited thereto, methylene, ethylene, n-propylene, n-butylene and the like.

The term "alkenylene" as used herein means a difunctional branched or unbranched hydrocarbon radical; in one aspect, having two to eight carbon atoms, and having at least one double bond, and includes, for example, and without being limited thereto, ethenylene, n-propenylene, n-butenylene and the like.

The term "alkynylene" as used herein means a difunctional branched or unbranched hydrocarbon radical; in one aspect, having two to eight carbon atoms, and having at least one triple bond, and includes, for example, and without being limited thereto, ethynylene, n-propynylene, n-butynylene and the like.

The term "aryl", alone or in combination, as used herein means a carbocyclic aromatic system containing one or more rings wherein such rings may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl or acenaphthyl. The "aryl" group may have 1 to 4 substituents such as lower alkyl, hydroxyl, halo, haloalkyl, nitro, cyano, alkoxy, lower alkylamino and the like.

The term "heteroaryl", alone or in combination, as used herein means an aromatic system having at least one heteroatom selected from N, S and/or O and containing one or more rings wherein such rings may be attached together in a pendent manner or may be fused. In particular embodiments, heteroaryl is one, two or three rings. In one aspect, the heteroaryl has five to twelve ring atoms. The term "heteroaryl" encompasses heteroaromatic radicals such as pyridyl, indolyl, furyl, benzofuryl, thienyl, benzothienyl, quinolyl, oxazolyl and the like. The "heteroaryl" group may have 1 to 4 substituents such as lower alkyl, hydroxyl, halo, haloalkyl, nitro, cyano, alkoxy, lower alkylamino and the like.

It is understood that substituents and substitution patterns on the compounds disclosed herein may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon or on different carbons, as long as a stable structure results.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula II or any of its intermediates. Illustrative inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula II for laboratory use, or for subsequent conversion to a pharmaceutically acceptable acid addition salt.

A "pharmaceutically acceptable basic addition salt" is any non-toxic organic or inorganic base addition salt of the acid compounds represented by Formula II or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" generally means a compound of Formula II or the pharmaceutically acceptable salt of a compound of Formula II wherein molecules of a suitable solvent are incorporated in a crystal lattice. A suitable solvent is physiologically tolerable at the dosage administered as the solvate. Examples of suitable solvents, but are not limited thereto, are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

In some embodiments, the therapeutic agent may be a peptide or polypeptide (or an active derivative, fragment or variant thereof) that activates the insulin signaling pathway in muscle tissue characterized by defective insulin signaling. For example, the peptide or polypeptide may activate or upregulate AMPK or AKT, or may inhibit JNK.

The terms "polypeptide" and "peptide," as used herein, refer to a sequence of amino acid residues linked together by peptide bonds or modified peptide bonds. Typically, a polypeptide is at least six amino acids long and a peptide is at least 3 amino acids long. The polypeptide or peptide can be naturally occurring, recombinant, synthetic, or a combination of these. The polypeptide or peptide can be a fragment of a naturally occurring protein or polypeptide. The terms polypeptide and peptide also encompass peptide derivatives, peptide analogues, and peptidomimetic compounds. Such compounds are well known in the art.

A "peptide derivative" is a peptide containing additional chemical or biochemical moieties not normally a part of a naturally occurring peptide. Peptide derivatives include peptides in which one or more amino acid side chain and/or the amino-terminus and/or the carboxy-terminus has been derivatized with a suitable chemical substituent group, as well as cyclic peptides, dual peptides, multimers of the peptides, peptides fused to other proteins or carriers glycosylated peptides, phosphorylated peptides, peptides conjugated to lipophilic moieties and peptides conjugated to an antibody or other biological ligand.

A "peptide analogue" is a peptide comprising one or more non-naturally occurring amino acids.

Peptidomimetics are compounds that are structurally similar to peptides and contain chemical moieties that mimic the function of the polypeptide or peptide of the present disclosure.

One skilled in the art will appreciate that not all amino acids in a peptide or polypeptide need be modified. Similarly not all amino acids need be modified in the same way. Polypeptide/peptide derivatives, analogues and peptidomimetics of the present disclosure thus include chimeric molecules that contain two or more chemically distinct regions, each region comprising at least one amino acid or modified version thereof.

A variant polypeptide or peptide is one in which one or more amino acid residues have been deleted, added or substituted for those that appear in the amino acid sequence of the naturally occurring protein. In the context of the present disclosure, a variant also retains substantially the same activity as the naturally occurring protein. Typically, when a variant contains one or more amino acid substitutions, they are "conservative" substitutions. A conservative substitution involves the replacement of one amino acid residue by another residue having similar side chain properties.

In accordance with the present disclosure, a polypeptide or peptide analogue, derivative, variant or active fragment has substantially the same or increased activity as compared to a naturally occurring target protein. The term "substantially identical activity" indicates an activity that is at least about 50%, more typically at least about 60%, 75%, 80%, 90% or 99% of the activity of a naturally occurring protein. In still another embodiment, the analogue, derivative, variant or active fragment exhibits enhanced (increased) activity compared to a naturally occurring protein, preferably a human protein.

As used herein, the term "about" refers to a +/−5% variation from the nominal value.

The polypeptides can be prepared by methods known in the art, such as purification from cell extracts or the use of recombinant techniques.

Shorter sequences can also be chemically synthesized by methods known in the art including, but not limited to, exclusive solid phase synthesis, partial solid phase synthesis, fragment condensation or classical solution synthesis (Merrifeld (1963) Am. Chem. Soc. 85:2149; Merrifeld (1986) Science 232:341). The polypeptides for use in accordance with the present disclosure can be purified using standard techniques such as chromatography (e.g. ion exchange, affinity, and sizing column chromatography or high performance liquid chromatography), centrifugation, differential solubility, or by other techniques familiar to a worker skilled in the art.

The polypeptides can also be produced by recombinant techniques. Typically this involves transformation (including transfection, transduction, or infection) of a suitable host cell with an expression vector comprising a polynucleotide encoding the protein or polypeptide of interest. For example, the nucleic acid sequences for human JNK1 and AMPK genes and various other components involved in the insulin signaling pathway are known in the art. These may be used as a basis for making the polynucleotides.

The polynucleotides can be derived or purified from a suitable source by standard techniques. The polynucleotides can be genomic DNA or RNA or they can be cDNA prepared from isolated mRNA. Alternatively, the known sequences may be used to prepare probes to obtain other nucleic acid sequences encoding the polypeptide from various sources using standard techniques.

Polynucleotides encoding fragments or variants of the naturally occurring proteins of interest can be constructed by deletion, addition, and/or substitution of one or more nucleotides within the coding sequence using standard techniques, such as site-directed mutagenesis techniques.

The polypeptides and peptides can also be produced as fusion proteins. One use of such fusion proteins is to improve the purification or detection of the polypeptide or peptide.

Specific initiation signals may be required for efficient translation of cloned polynucleotide. These signals include the ATG initiation codon and adjacent sequences. In cases where an entire wild-type gene or cDNA, including its own initiation codon and adjacent sequences, is inserted into the appropriate expression vector, additional translational control signals may not be needed. In other cases, exogenous translational control signals, including, perhaps, the ATG initiation codon, must be provided.

Furthermore, the initiation codon must be in phase with the reading frame of the desired coding sequence to ensure translation of the entire insert. The exogenous translational control signals and initiation codons can be natural or synthetic. The efficiency of expression may be enhanced by the inclusion of appropriate transcription enhancer elements and/or transcription terminators (Bittner et al. (1987) Methods in Enzymol. 153, 516).

Signal sequences may also be incorporated into the molecules for targeting of the expressed polypeptides or peptides.

Suitable expression vectors for use with the nucleic acid sequences include, but are not limited to, plasmids, phagemids, viral particles and vectors, phage and the like. For insect cells, baculovirus expression vectors are suitable. For plant cells viral expression vectors (such as cauliflower mosaic virus and tobacco mosaic virus) and plasmid expression vectors (such as the Ti plasmid) are suitable. The entire expression vector, or a part thereof, can be integrated into the host cell genome. In some circumstances, it is desirable to employ an inducible expression vector as known in the art. In some circumstances, it is desirable to employ an inducible expression vector, e.g. the LACSWITCH Inducible Expression System (Stratagene, LaJolla, Calif.).

Those skilled in the field of molecular biology will understand that a wide variety of expression systems can be used to provide the recombinant polypeptide or peptide. The precise host cell used is not critical. The polypeptide or peptide can be produced in a prokaryotic host (e.g., E. cold or B. subtilis) or in a eukaryotic host (e.g., Saccharomyces or Pichia; mammalian cells, such as COS, NIH 3T3, CHO, BHK, 293, or HeLa cells, insect cells, or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, e.g. in Cloning Vectors: A Laboratory Manual (Ponwels et al., 1985, Supp. 1987) and by various commercial suppliers.

In addition, a host cell may be chosen which modulates the expression of the inserted sequences, or modifies and processes the gene product in a specific, desired fashion. Such modifications (e.g. glycosylation) and processing (e.g. cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed heterologous protein.

The host cells harboring the expression vehicle can be cultured in conventional nutrient media adapted as needed for activation of a chosen gene, repression of a chosen gene, selection of transformants, or amplification of a chosen gene according to known procedures.

The present disclosure also contemplates antisense oligonucleotides to various genes of interest, for example, JNK1. In one embodiment, the therapeutic agent is a JNK1 antisense oligonucleotide Inhibition of JNK, which inhibits the insulin-signaling pathway, would indirectly activate the pathway by restoring the response to insulin.

The present disclosure also contemplates oligonucleotide modulators that are short interfering double-stranded RNA molecules (siRNAs). RNA interference mediated by siRNAs is known in the art to play an important role in post-transcriptional gene silencing [Zamore, Nature Struc. Biol., 8:746-750 (2001)] In nature, siRNA molecules are typically 21-22 base pairs in length and are generated when long double-stranded RNA molecules are cleaved by the action of an endogenous ribonuclease. Recently, it has been demonstrated that transfection of mammalian cells with synthetic siRNA molecules having a sequence identical to a portion of a target gene leads to a reduction in the mRNA levels of the target gene.

The oligonucleotide modulators can be prepared by conventional techniques well-known to those skilled in the art. For example, the oligonucleotides can be prepared using solid-phase synthesis using commercially available equipment, such as the equipment available from Applied Biosystems Canada Inc. (Mississauga, Canada).

Alternatively, the oligonucleotide modulators can be prepared by enzymatic digestion and/or amplification of the naturally occurring target gene or mRNA, or of cDNA synthesized from the mRNA, using standard techniques known in the art.

When the oligonucleotide inhibitors comprise RNA, they can be prepared by in vitro transcription methods also known in the art. As indicated above, siRNA molecules can also be conveniently prepared using commercially available in vitro transcription kits. Oligonucleotides can also be prepared using recombinant DNA techniques.

In some embodiments, the therapeutic agent is an antidiabetic agent selected from the group consisting of insulin, insulin mimetics, and insulin secretagogues. Non-limiting examples of antidiabetic agents include insulin, insulin mimetics, insulin analogues, biguanides (e.g. metformin, phenformin), meglitinides (e.g. repaglinide, nateglinide), biguanide/glyburide combinations (e.g., Glucovance®), insulin secretagogues, incretins, insulin sensitizers (e.g., metformin, glitazones, and thiazolidinediones), sulfonylureas (e.g., glimepiride, glyburide, gliclazide, chlorpropamide, glipizide, gliamilide, acetohexamide, glibenclamide, tolazamide, and tolbutamide), thiazolidinediones (e.g., troglitazone, rosiglitazone and pioglitazone).

In some embodiments, the insulin secretagogue is a sulfonylurea or a meglitinide. In some embodiments, the antidiabetic agent is selected from insulin, an insulin analogue, a co-secreted agent, pramlinitide, and a DPP4 antagonist.

In some embodiments, the anti-diabetic drug may be a PPAR-a agonist, PPAR-y agonist, or PPAR-a/y dual agonist. However, there have been reported cardiac problems with such compounds and, given that dystrophy patients are known to have cardiac complications, patients would have to be closely monitored for potential cardiac issues.

In some embodiments, the therapeutic agent is a an insulin sensitizers (e.g., metformin, glitazone, and thiazolidinedione).

In some embodiments, the therapeutic agent is a modulator of insulin signaling. The term "modulator" as used herein refers to both activators and inhibitors of a signaling event. The modulator may include, for example, any drug that improves insulin resistance and/or enhances muscle metabolism. Modulators may, for example, include activators of insulin signaling.

The therapeutic agents disclosed herein may be administered alone but, more typically, will be incorporated into a composition for the treatment and/or prevention of a muscle condition or disease characterized by impaired insulin-dependent signaling. Pharmaceutical compositions and methods of preparing them are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000).

Thus, in accordance with the present disclosure, there are contemplated compositions for the treatment and/or prevention of a muscle condition or disease characterized by impaired insulin-dependent signaling. The compositions comprise one or more therapeutic agents that act, at least in part, by activating the insulin signaling pathway, which is now known to be impaired in certain muscle diseases and conditions. The therapeutic agent may be any one or more of the therapeutic agents described herein.

The pharmaceutical composition may comprise one or more therapeutic agents, or active ingredients, together with one or more pharmaceutically acceptable diluents, carriers or excipients. A "pharmaceutically acceptable" diluent, carrier or excipient is a material that is mixed with the therapeutic agent in order to permit the formation of a pharmaceutical composition, i.e., a dosage form capable of administration to a patient, the material being generally non-toxic when administered to a patient. Pharmaceutically acceptable diluents, carriers, and excipients are well known to those of skill in the art. Furthermore, a skilled person can formulate a suitable combination of pharmaceutically acceptable carriers, diluents and/or excipients depending on, for example, the properties of the therapeutic agent, their concentration in the composition, the dosage form, and the route of administration, among other factors.

The composition may comprise one or more additional therapeutic agents. In some embodiments, the additional therapeutic agent comprises an agent for promoting muscle regeneration or repair. For example, the composition may comprise one or more stem cell modulators, one or more muscle stem cells, or a combination thereof.

In some embodiments, the additional therapeutic agent is a corticosteroid (e.g., prednisone, prednisolone or deflazacort, dexamethasone, among others). Corticosteroids are currently the first-line therapy for certain muscle diseases, e.g. muscular dystrophies, and it is expected that the combination of a corticosteroid with a therapeutic agent that activates the insulin signaling pathway would provide significant benefit to patients.

Corticosteroids include natural and synthetic compounds having glucocorticoid and/or mineralocorticoid activity. Natural corticosteroids are synthesized from cholesterol within the adrenal cortex. Synthetic drugs with corticosteroid-like effect are used to treat a variety of conditions and diseases. Dexamethasone and its derivatives are almost pure glucocorticoids, while prednisone and its derivatives have some mineralocorticoid action in addition to the glucocorticoid effect. Deflazacort, a prodrug with glucocorticoid properties, has approximately 70-90% potency compared to prednisone.

In some embodiments, the corticosteroid is prednisone. In some embodiments, the corticosteroid is prednisolone. In some embodiments, the corticosteroid is deflazacort. In some embodiments, the corticosteroid is dexamethasone.

The optimal dosage of corticosteroid, when used in combination with a therapeutic agent that activated the insulin signaling pathway, can be determined by a person of skill in the art, for example, by titration.

Where multiple therapeutic agents are to be administered, they may be administered together or separately. For example, they may be administered together in a single composition, together in separate compositions, or separately in separate compositions. In some embodiments, a single composition comprises two or more therapeutic agents. In one embodiment, a single composition comprises metformin and a corticosteroid (e.g. one or more of prednisone, prednisolone, deflazacort, or dexamethasone). In another embodiment, metformin and a corticosteroid are comprised in two separate compositions. The metformin may be administered prior to, concurrently with, or subsequent to the corticosteroid in a combination therapy.

Administration of the pharmaceutical compositions disclosed herein may be by any of a number of routes depending upon whether local or systemic treatment is desired, and upon the area to be treated. In some embodiments, the compositions are administered locally. In some embodiments, the compositions are administered systemically.

Where multiple therapeutic agents are to be administered, they may be administered by the same or different routes of administration.

The pharmaceutical composition may be formulated, for example, for enteral administration, topical administration, parenteral administration, or pulmonary administration.

Enteral administration may comprise, for example, oral, sublingual, rectal or vaginal administration. In some embodiments, the composition is for oral administration. For the oral mode of administration, the compositions may be formulated in the form of tablets, capsules, lozenges, chewing gum, troches, powders, syrups, elixirs, aqueous solutions and suspensions, and the like. In the case of tablets, carriers may be used, including, for example, lactose, sodium citrate and salts of phosphoric acid. Various disintegrants, such as starch, and lubricating agents such as magnesium stearate and talc, are also commonly used in tablets. For oral administration in capsule form, useful diluents include, for example, lactose and high molecular weight polyethylene glycols. If desired, certain sweetening and/or flavoring agents can be added.

Parenteral administration may comprise, for example, intramuscular, subcutaneous, intravenous, intrarterial, intracerebral, intraperitoneal, intracardiac, intrathecal or intraosseous administration. In some embodiments, the parenteral administration is intramuscular administration. In some embodiments, the parenteral administration is subcutaneous administration. In some embodiments, the parenteral administration is intravenous administration. In some embodiments, compositions are administered by injection or infusion. For parenteral administration, sterile solutions are usually prepared, and the pHs of the solutions are suitably adjusted and buffered. For intravenous use, the total concentration of solutes should be controlled to render the preparation isotonic.

The compositions for parenteral administration can be administered, for example, by injection as a solution or suspension in a pharmaceutically acceptable liquid medium, e.g. oil or aqueous medium or emulsion. Alternatively, the composition can be administered in a biocompatible medium which is, or becomes in site, a semi-solid or solid matrix. For example, the matrix maybe an injectable liquid which forms a semi-solid gel at the site of tissue damage or degeneration, such as matrices comprising collagen and/or its derivatives, polylactic acid or polyglycolic acid, or it may comprise one or more layers of a flexible, solid matrix that is implanted, such as impregnated fibrous matrices. Such matrices are known in the art (for example, Gelfoam available from Upjohn, Kalamazoo, Mich.) and may act to hold the active ingredients in place at a target location. In some embodiments, parenteral administration may include the use of a pump for periodic or continuous delivery.

In some embodiments, the composition is formulated for topical administration. Topical administration may include, for example, delivery via the skin or the mucous membranes of, for example, the eyes, nose, urethra, rectum or vagina. The topical composition may be in the form of, for example, a cream, lotion, gel, paste or ointment. In some embodiments, topical administration, may include, for example, the use of a patch or other transdermal delivery device. For ocular administration, ointments or droppable liquids may be delivered by ocular delivery systems known to the art such as applicators or eye droppers. Suppository dosage forms are useful for vaginal, urethral and rectal administration. Such suppositories will generally be constructed of a mixture of substances that is solid at room temperature but melts at body temperature. The substances commonly used to create such vehicles include the obroma oil, glycerinated gelatin, hydrogenated vegetable oils, mixtures of polyethylene glycols of various molecular weight and fatty acid esters of polyethylene glycol. Analogous gels or creams can be used for vaginal, urethral and rectal administrations.

In some embodiments, the composition is for administration by pulmonary route, for example, by inhalation or insufflation of powders or aerosols, for example, using a nebulizer. For aerosol administration, diluents and/or carriers selected will be appropriate to allow the formation of an aerosol. In some embodiments, the composition is for intranasal administration.

The compositions described herein may be delivered in combination with a pharmaceutically acceptable vehicle. Preferably, such a vehicle would enhance the stability and/or delivery properties. Numerous administration vehicles will be apparent to those of ordinary skill in the art, including without limitation, slow release formulations, liposomal formulations, microparticles, microcapsules and polymeric matrices.

In some embodiments, the composition comprises a pharmaceutically acceptable acid addition salt or a pharmaceutically acceptable base addition salt. Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts include those derived from non-toxic metals such as sodium or potassium, ammonium salts and organo-amino salts such as triethylamine salts. Numerous appropriate such salts will be known to those of ordinary skill.

The dosage regimen for a composition as disclosed herein may be selected or optimized n accordance with a variety of factors including type, species, age, weight, sex and medical condition of the patient; the severity of the condition to be treated; the route of administration; the renal and hepatic function of the patient; and the particular therapeutic agent(s) being administered. A physician or veterinarian of ordinary skill can readily determine and prescribe the effective amount of the therapeutic agent or composition required to treat and/or prevent the disease or condition characterized by impaired insulin dependent signaling. Where a standard dosage is not known, treatment will generally be initiated with small dosages less than the optimum dose of each therapeutic agent. Thereafter, the dosage is increased until the optimum effect under the circumstances is reached. In general, the pharmaceutical compositions are administered at a concentration that will generally afford effective results without causing harmful or deleterious side effects. Administration can be either as a single unit dose or, if desired, the dosage can be divided into convenient subunits that are administered at suitable times throughout the day.

In general, dosages are often selected to maintain a serum level of the therapeutic agent between about 0.01 µg/cc and about 1000 µg/cc, or between about 0.1 µg/cc and about 100 µg/cc. For parenteral administration, an alternative measure of administration amount is from about 0.001 mg/kg to about 10 mg/kg (e.g. from about 0.01 mg/kg to about 10 mg/kg), or from about 0.01 mg/kg to about 1 mg/kg (e.g. from about 0.1 mg/kg to about 1 mg/kg), will be administered. For oral administration, an alternative measure of administration amount is from about 0.001 mg/kg to about 10 mg/kg (e.g. from about 0.1 mg/kg to about 10 mg/kg), or from about 0.01 mg/kg to about 1 mg/kg (e.g. from about 0.1 mg/kg to about 1 mg/kg). For administration in suppository form, an alternative measure of administration amount is from about 0.1 mg/kg to about 10 mg/kg, e.g. from about 0.1 mg/kg to about 1 mg/kg.

Thus, in another aspect, the present disclosure contemplates methods for the prevention and/or treatment of a muscle condition or disease characterized by impaired insulin-dependent signaling. The treatment methods may be applied to any muscle disease or condition that is characterized by the signaling defect.

In some embodiments, the method comprises administering to a subject in need thereof a therapeutic agent as described herein. A subject in need thereof may be a subject that has, is suspected of having, or is at risk of developing a muscle disease or condition characterized by impaired insulin-dependent signaling. The therapeutic agent preferably activates the insulin signaling pathway downstream of IRS-1, either directly or indirectly, thereby targeting the underlying signaling defect in the muscle tissue.

The term "treat" or "treating" generally means to alleviate symptoms or pathology of a muscle disease or condition characterized by impaired insulin-dependent signaling, eliminate the causation of the symptoms or pathology, either on a temporary or permanent basis, or to inhibit or delay the onset of symptoms or pathology of the named disease or condition.

The term "prevent" generally means to inhibit or delay the onset of symptoms or pathology of a muscle disease or condition characterized by impaired insulin-dependent signaling.

The term "therapeutically effective amount" means an amount of the therapeutic agent which is effective in treating or preventing the named disorder or condition without eliciting significant adverse effects.

Tests can be performed by those of skill in the art, including those tests described in the Examples section, to determine whether a given muscle disease or condition is characterized by defective insulin signaling in muscle tissue, and also to determine whether a particular patient would benefit from a treatment method disclosed herein.

Correction of the underlying signaling defect may result in one or more of the following: reduced clinical pathology, reduced symptoms, delayed onset or progression of disease, enhanced mobility, increased muscle mass, increased muscle strength, improved contractile properties, increased muscle regeneration, increased repair of damaged or defective tissue, and/or prevention of muscle atrophy.

The selected therapeutic agent or composition may be administered as a monotherapy or as part of a combination therapy. In some embodiments, the therapeutic agent is administered in a monotherapy. In other embodiments, the therapeutic agent for activating the insulin signaling pathway is administered as part of a combination therapy with another therapeutic agent, in particular, a therapeutic agent that targets other pathways. Some overlap in the pathways targeted is, of course, permitted.

In some embodiments, method comprises administration of metformin or an analogue or derivative thereof, in a combination therapy. For example, metformin may be co-administered with a corticosteroid, such as prednisone, prednisolone, deflazacort, or dexamethasone, among others. The corticosteroid may be administered to the subject prior to, concurrently with, or subsequent to the therapeutic agent.

The combination therapy with metformin is expected to provide a significant advantage in that standard therapeutic doses of corticosteroids may be reduced, thereby reducing the side effects associated with these drugs. It is predicted, for example, that corticosteroid treatment in combination with metformin treatment will provide an effective combinatorial drug regime to treat DMD and related diseases.

Evaluation of the therapeutic agents described herein may be accomplished through in vitro, ex vivo and/or in vivo assays that are well known in the art, including the assays described below. Additionally, various screening methods known in the art can be employed to identify candidate activators of the insulin signaling pathway. For example, activators that up- or down-regulate a target gene can be identified by monitoring cells treated with the candidate activator for an increase or decrease in the expression of the target gene. Methods such as Northern blot analysis, quantitative RT-PCR or microarray analysis can be used for this purpose. Alternatively, an increase or decrease in the corresponding protein level can be monitored, for example, by Western blot analysis. Activators or inhibitors that modulate the activation state of a signaling molecule, e.g. phosphorylation state, can also be identified using appropriate assays. For polypeptide or peptide activators (or analogues, derivatives, variants or peptidomimetic compounds corresponding to the polypeptides) that bind a specific protein, the binding ability can be determined using one of a variety of binding assays known in the art (see, for example, Coligan et al., (eds.) Current Protocols in Protein Science, J. Wiley & Sons, New York, N.Y.). For antibody or antibody fragment activators, various immunoassays can be used.

The ability of potential therapeutic agents to rescue tissue from impaired insulin dependent signaling, or to improve behavioral outcomes, can be tested in a suitable animal model. One well-established animal model of muscular dystrophy is the mdx mouse model. There are other available mouse models of muscular dystrophy besides the mdx mouse model. Mouse models for congenital MD include the dy/dy (dystrophia-muscularis) mouse and the allelic mutant dy(2J)/dy(2J) mouse, both presenting significant reduction of alpha2-laminin in the muscle and a severe phenotype. The myodystrophy mouse (Large(myd)) harbors a mutation in the glycosyltransferase Large, which leads to altered glycosylation of alpha-DG, and also a severe phenotype. More recently, using the homologous recombination technique in embryonic stem cell, several mouse models have been developed with null mutations in each one of the four SG genes. All sarcoglycan-null animals display a progressive muscular dystrophy of variable severity and share the property of a significant secondary reduction in the expression of the other members of the sarcoglycan subcomplex and other components of the Dystrophin-glycoprotein complex. Other informative models for muscle proteins include the knockout mouse for myostatin, which demonstrated that this protein is a negative regulator of muscle growth. Additionally, the stress syndrome in pigs, caused by mutations in the porcine RYR1 gene, helped to localize the gene causing malignant hypertermia and Central Core myopathy in humans.

The canine golden retriever MD model (the best characterized dog model), the disease results from a single base pair change in the 30 consensus splice site of intron 6, leading to skipping of exon 7 and alteration of the reading frame in exon 8, which creates a premature stop (Sharp N J, et al. *Genomics* 1992 13(1):115-121). This model represents a clinically similar model of DMD due to the large size of the animal and significant muscle weakness. Autosomal recessive limb-girdle MD forms models include the SJL/J mice, which develop a spontaneous myopathy resulting from a mutation in the Dysferlin gene, being a model for LGMD2B. For the human sarcoglycanopahties (SG), the BIO14.6 hamster is the spontaneous animal model for delta-SG deficiency, whereas some canine models with deficiency of SG proteins have also been identified (Willmann R. et al. Neuromuscular Disorders 2009 19 241-249; Vainzof M. et al. J Mol Neurosci. 2008 34(3):241-8).

These and other animal models may be used to investigate impairments in insulin signaling in various forms of muscle disease and the effects of therapeutic agents. Activators of the insulin signaling pathway, such as metformin and analogues and derivatives thereof, are expected to provide benefit in forms of disease characterized by impaired insulin-dependent signaling.

The ability of the compound(s) and treatments to repair damaged muscle tissue can be tested, for example, by administering the compound(s) or treatments to mice exposed to freeze-induced or cardiotoxin-induced muscle damage, and monitoring repair of the damaged muscle (see Megeney et al., (1996) Genes Dev., 10:1173-1183; Asakura et al., (2000) J: Cell Biol., 159:123-134).

In another aspect, there is provided a method of determining whether a subject suffering from a muscle disease or condition would benefit from treatment with an activator of the insulin signaling pathway. The method comprises obtaining a biological sample from the subject; and testing the sample for impaired insulin dependent signaling, wherein the identification of impaired insulin dependent signaling is indicative that the patient would benefit from treatment with an activator of the insulin signaling pathway. The sample may be, for example, a cell or tissue sample. The cell or tissue may be blood-derived or muscle-derived. In some embodiments, the sample is a muscle cell or muscle tissue.

In another aspect, there are provided commercial packages and kits comprising the therapeutic agents and/or compositions disclosed herein.

The commercial packages or kits may comprise one or more therapeutic agents together with instructions for use in the prevention and/or treatment of a muscle disease or condition characterized by impaired insulin dependent signaling.

In some embodiments, therapeutic kits are provided comprising one or more therapeutic agents in pharmaceutical compositions.

In some embodiments, the kit is a diagnostic kit, for example, to identify a patient that may benefit from treatment with a particular therapeutic agent or composition.

Individual components of the kit could be packaged in separate containers and, associated with such containers, can be a notice in the form prescribed by a governmental agency regulating the manufacture, use or sale of pharmaceuticals or biological products, which notice reflects approval by the agency of manufacture, use or sale for human or animal administration.

When the components of the kit may be provided in one or more liquid solutions, the liquid solution can be an aqueous solution, for example, a sterile aqueous solution. In this case, the container means may be a sealed pouch or vial, an inhalant, syringe, pipette, eye dropper, or other such like apparatus, from which the composition may be administered to a patient.

The components of the kit may also be provided in dried or lyophilized form and the kit can additionally contain a suitable solvent for dissolution or reconstitution of the components. Irrespective of the number or type of containers, the kits also may comprise an instrument for assisting with the administration of the composition to a patient.

In other aspects, there are provided uses of the therapeutic agents and compositions disclosed herein for the treatment and/or prevention of a muscle disease or condition characterized by impaired insulin dependent signaling. In some embodiments, there is provided a use of a therapeutic agent disclosed herein for the manufacture of a medicament for the treatment and/or prevention of a muscle disease or condition characterized by impaired insulin dependent signaling.

Discussion of Experimental Findings

This section is a discussion of insulin signaling as it relates to the experimental findings described below in the Examples. The scope of the invention is not intended to be limited by the content of this discussion, which is merely provided to aid the reader in understanding the present disclosure.

A schematic representation of insulin-dependent signaling pathways is shown in FIG. 1. Following the binding of insulin to its cognate receptor, the receptor is subject to tyrosine autophosphorylation, which recruits and activates adapter/signaling proteins such as IRS-1. IRS-1 serves as a focal point for the activation of multiple insulin-dependent signaling cascades, i.e. as a major docking site for phosphatidylinositol 3-kinase (PI 3 kinase), which in turn promotes the recruitment of various kinases to membrane locations (AKT) followed by their activation (reviewed in White et al. 2002). AKT activation is known to act as a prerequisite for insulin-stimulated glucose transport through the recruitment and translocation of the insulin regulated glucose transporter protein, GLUT4, from intracellular storage membranes to the plasma membrane proper, although the precise mechanism remains unknown (Lizcano and Alessi 2002). In addition, IRS-1/AKT signaling has been established as a crucial pro-survival pathway in skeletal muscle (Sandri et al. 2004; Stitt et al. 2004) and one study has reported that AKT phosphorylation may protect myotube integrity against the loss of dystroglycan function in vitro (Langenbach and Rando et al. 2002).

The progression of disease pathology in the dystrophic mdx mouse has been associated with constitutive activation of the MAP Kinase, JNK1 (Kolodziejczyk et al. 2001), a ubiquitous signaling molecule. In the present studies, it was postulated that the increased activity of JNK1 in dystrophic muscle could be suggestive of metabolic perturbations, since elevated JNK1 activity in skeletal muscle is known to be a key event in the development of insulin resistance in diabetes (Hirosumi et al. 2002; Chung et al. 2008). Studies were thus conducted to test the hypothesis that dystrophic skeletal muscle has a disruption in normal metabolic function and that this deficit exacerbates the disease pathology. In looking to other effectors of insulin signaling, two recent studies were identified that demonstrated that a transgenic strain overexpressing AKT, a ubiquitous signaling intermediate, bred to the mdx background alleviated the dystrophic pathology associated with the mdx strain (Peter et al. 2009), while improving contractile parameters (Blaauw et al. 2008). However, this finding on its own does not implicate an underlying defect in insulin signaling. The interpretation of these observations was that elevation of AKT signaling restored the expression of utrophin and DGC components leading to a reduction in muscle pathology (Peter et al. 2009). Although the metabolic status of the combinatorial transgenic strain was not investigated, the present inventors now postulate that the phenotypic correction may have derived, at least in part, from a correction in an underlying metabolic disturbance.

In general, IRS-1 is subject to inhibitory serine phosphorylation or activating tyrosine phosphorylation (Y941). JNK1 can directly phosphorylate the IRS-1 protein at serine 307 leading to inhibition of insulin signaling (Aguirre et al. 2000; Hilder et al. 2004). It is demonstrated herein that JNK1 targets and phosphorylates the insulin receptor substrate IRS-1 at serine 307 in dystrophic muscle with attendant disruptions in insulin mediated signal events and insulin sensitive metabolic responses. This serine phosphorylation of IRS-1 is known from the literature to induce insulin resistance and metabolic disturbance in a variety of diabetes-related conditions and obesity. As such, the present inventors postulated that dystrophic skeletal muscle may suffer from similar metabolic limitations. In carrying out their studies, the inventors have now determined that dystrophic myofibers are indeed characterized by metabolic perturbations, including loss of glycogen content, altered distribution of the insulin sensitive glucose transporter protein GLUT4 and inhibition in key metabolic regulatory factors such as AKT, AMPK etc., all of which are consistent with an insulin resistant state.

Based on these observations, the inventors postulated that dystrophic muscle pathology may be attenuated by use of compounds or drugs that treat or alleviate insulin resistance. The most commonly prescribed drug for treating insulin resistance in Type II diabetes is metformin. To test this hypothesis, the impact of metformin delivery in dystrophic mice (the mdx model) was explored. Metformin was continuously delivered for either a 14-day or 28-day period via the use of implanted osmotic mini-pumps (Alzet minipumps). The animals were closely monitored throughout the study for adverse events and at the end of the indicated time period, animals were euthanized and a variety of skeletal muscles were collected and analyzed for dystrophic muscle characteristics. Metformin-treated animals displayed a significant correction in the dystrophic muscle phenotype. For example, metformin treatment led to a reduction in myofiber damage, reduced numbers of centrally located myonuclei (indicative of degenerating and regenerating myofibers), restoration of glycogen concentrations, normal distribution of GLUT4 and upregulation in the metabolic regulatory kinase AKT and down regulation of the catabolic kinase GSK3β.

Thus, these findings demonstrate that dystrophy patients may derive significant benefit from a metformin treatment regime. Moreover, any compound that improves skeletal muscle insulin resistance may be useful as a treatment for Duchenne muscular dystrophy (DMD) and its related genetic disorders such as Becker's muscular dystrophy, limb girdle muscular dystrophies, among others.

The development of dystrophic muscle pathology has been understood to arise primarily from mechanical insufficiency, which in turn leads to increased susceptibility of the affected muscle fibers to work related damage. However, the work of the present inventors now indicates that dystrophic muscle also suffers from a general metabolic disturbance which itself may augment or accelerate the evolving pathology. Importantly, it has now been demonstrated that therapeutic agents that act to correct the underlying metabolic disturbance, such as metformin and its derivatives, can significantly limit the development of dystrophic muscle damage and improve behavioral outcomes, opening an exciting new avenue for therapeutic intervention. Furthermore, patients suffering from other muscle diseases and conditions characterized by impaired insulin-dependent signaling may also derive benefit from treatments that target the signaling defect.

EXAMPLES

Example 1

Inhibition of Insulin-Signaling in Dystrophic Skeletal Muscle

Figure 2:
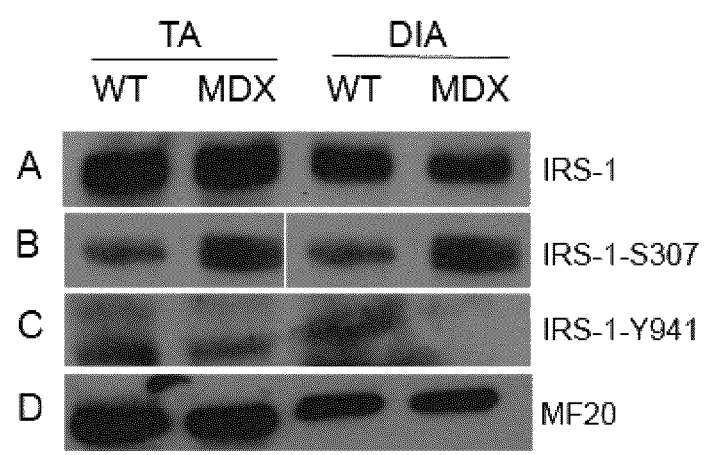
FIG. 2 illustrates that IRS-1 Serine Phosphorylation is Increased in Dystrophic Skeletal Muscle. Protein lysates were obtained from the tibialis anterior (TA) and diaphragm (DIA) muscles of 4, 8 and 10 wk old WT and MDX mice. Immunoblotting was performed using anti-IRS-1 (Row A), anti-IRS-1-S307 (Row B) and anti-IRS-1Y941 (Row C) to compare expression levels. (Row D) MF-20 was used as a loading control. (n=3).
Figure 3:
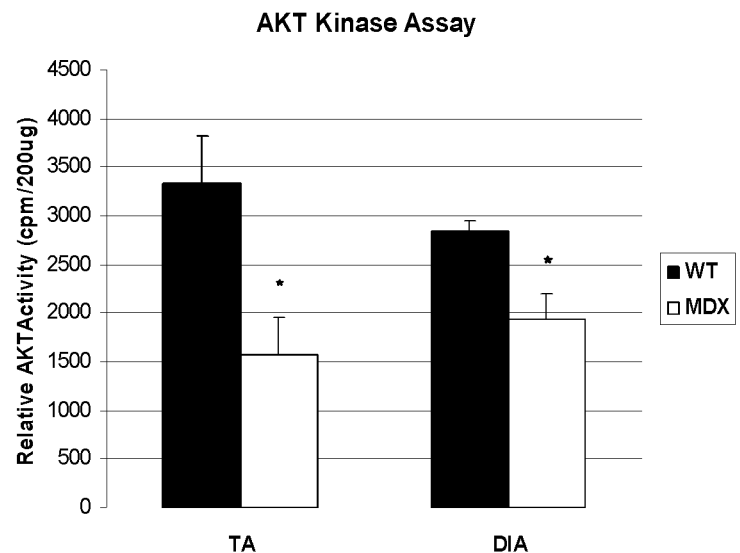
FIG. 3 illustrates that normal AKT phosphorylation and GSK-3β activity are altered in Dystrophic Skeletal Muscle. A) AKT was immunoprecipitated from skeletal muscles (TA and DIA) wild-type (WT) and MDX mice. AKT kinase assay was preformed using AKT substrate peptide and [γ-32P]ATP. Kinase reaction was dotted on p81 paper and radioactivity was measured by scintillation counter (mean+SE; n>3 *p<0.05). B) Active GSK-3β was immunoprecipitated and GSK-3β kinase assay was preformed using GSK-3β peptide substrate and [γ-32P]ATP. Kinase reaction was dotted on p81 paper and radioactivity was measured by scintillation counter (mean+SE; n>3 *p<0.05).
Figure 3:
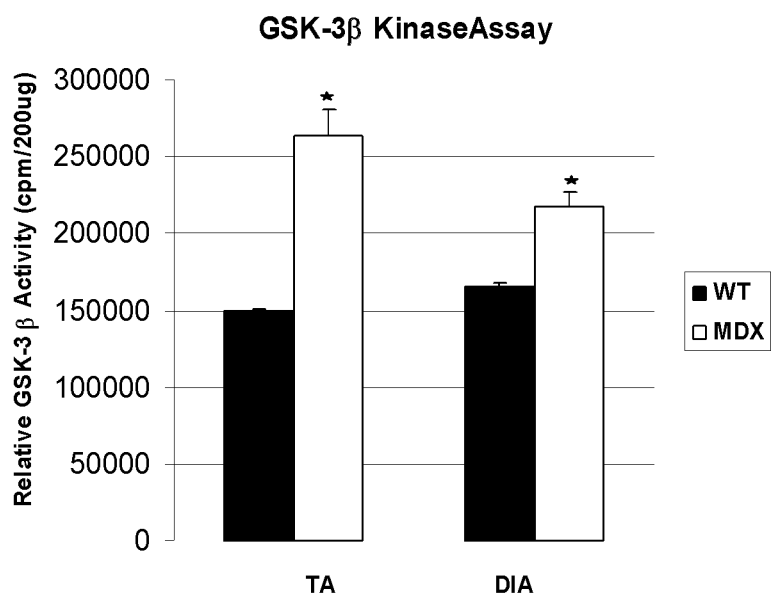

To begin to address the hypothesis that dystrophic muscle pathology develops (in part) from perturbations in metabolic control, the phosphorylation status of the insulin receptor substrate 1 (IRS-1) was measured in normal and mdx skeletal muscle. Importantly, western blot analysis revealed that dystrophic muscle exhibited a 3-fold increase in IRS-1 serine$^{307}$ phosphorylation, and a significant decrease in IRS-1 tyrosine$^{941}$ phosphorylation in the TA and DIA, respectively (FIG. 2, lanes B and C). Modifications in IRS-1 phosphorylation were not reflective of changes in total expression levels of IRS-1, which remained constant (lane A). These results suggested that insulin-mediated signal events may be compromised in dystrophic muscle through the activation of JNK1. Therefore, the activity of IRS-1 responsive signal components, AKT and GSK3β, were examined. Under normal circumstances, following insulin stimulation, AKT becomes activated, leading to the subsequent inhibition of GSK-3β activity. Additionally, the allosteric activation of AKT and GSK3β by GSK-3 and GS, respectively has been well established. Thus, to examine the relative contributions of these factors, kinase activity in skeletal muscle from wild-type (WT) and mdx animals was analyzed. AKT kinase activity was significantly decreased by ~53% (TA) and ~33% (DIA) in dystrophic muscle compared to wild-type muscles (FIG. 3A). Consequently, GSK-3β kinase activity was elevated by ~45% (TA) and ~24% (DIA) in mdx animals compared to wild-type control animals (FIG. 3B). These changes in kinase activity are consistent with an inhibition of insulin/IRS-1 signaling (See FIG. 1) and suggest that the activity of downstream metabolic regulatory factors is altered in dystrophic skeletal muscle. Taken together, these observations imply that dystrophic skeletal muscle suffers from an inherent metabolic deficiency that may arise from inhibition or reduction in insulin-mediated signaling events.

These data imply that JNK1 antagonizes insulin signaling in dystrophic mdx skeletal muscle. As such, insulin mimetics, particularly those that act downstream of the insulin receptor, may provide an amenable therapeutic intervention to circumvent or limit the signaling defects seen in dystrophic muscle to thereby alleviate the pathology or progression of the dystrophic muscle phenotype. Although insulin itself may provide an effective mechanism to curtail dystrophic muscle pathology, exogenous insulin may be insufficient to counteract the degree of inhibitory IRS1 serine 307 phosphorylation. It is also possible that the insulin dose required for efficacy would induce hypoglycemia.

Example 2

Glycogen Deposition and Glut4 Translocation are Altered in Dystrophic Muscle

Figure 5:
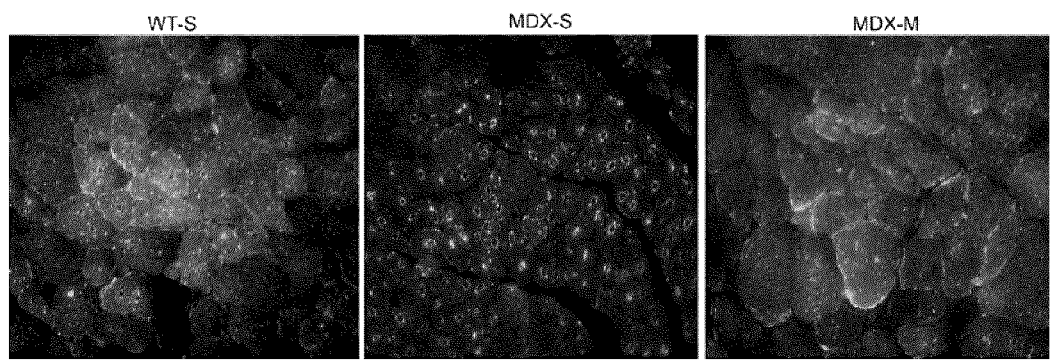
FIG. 5 illustrates that Metformin Treatment Restores GLUT4 Localization in Dystrophic Skeletal Muscle. Immuno-histochemistry on paraffin sections of the TA muscles of WT and MDX (saline and metformin treated) mice to analyze GLUT4 localization (green) using anti-GLUT4 antibody (1:200). (Magnification, 20×).

Given that dystrophic skeletal muscle displayed a significant inhibition of insulin/IRS-1 mediated signals, it was postulated that the metabolic status of the muscle would be similarly disrupted. In skeletal muscle, the vast majority of polymer glucose is stored as glycogen dispersed in granules. The present study therefore investigated glycogen deposition in wild-type and mdx skeletal muscles using periodic acid schiff staining. Under normal conditions, wild-type muscles show glycogen distributed uniformly throughout the cytoplasm of the myofiber. In contrast, dystrophic muscle revealed an asymmetrical distribution (pooling or loss) of glycogen content in the TA. Formation of glycogen stores is contingent on glucose uptake, a process dependent on the recruitment and translocation of the glucose transporter, GLUT4, which is mediated by insulin signaling. As such, the present study investigated whether defects in insulin signaling would reflect alterations in GLUT4 translocation in dystrophic (TA) muscle. Immunohistochemistry revealed that GLUT4 was localized predominantly in a perinuclear fashion in mdx muscles compared to wild-type control muscles (FIG. 5). The mis-localization of GLUT4 is consistent with repression of IRS-1 signals, as such, the observations of altered glycogen deposition and GLUT4 localization further confirmed the hypothesis that insulin-dependent signaling is impaired in dystrophic muscle.

Example 3

Metformin Treatment Improves the Metabolic Profile and Limits Pathology in Dystrophic Skeletal Muscle Based on the results in Examples 1 and 2, studies were conducted to determine whether an insulin mimetic would circumvent the signaling defect and alter the progression of the dystrophic muscle pathogenesis, thereby providing a novel pharmacologic intervention to treat or prevent dystrophic muscle pathology. The mimetic selected for testing was metformin. Metformin is a standard intervention for type 2 diabetes/insulin resistance and has a post-insulin receptor mode of action (reviewed in Musi and Goodyear 2006). Although metformin and its chemical derivatives have been in clinical use since 1957, the mode of action for this drug has remained unknown until the recent past. Metformin is known to stimulate cross-talk between insulin-dependent and insulin-independent signaling pathways, leading to substantial upregulation of AKT and AMPK kinase activities, respectively. Specifically, metformin stimulates the kinase AMPK and, once activated, AMPK activates many insulin-dependent cellular functions, such as enhancing glucose transport, restoring glycogen levels etc., through as yet undefined mechanisms (reviewed in Misra 2008; Zhou et al. 2001; Musi et al. 2002 Suwa et al. 2006). Since the molecular target of metformin lies downstream of the insulin receptor and IRS-1, it was predicted that metformin administration would effectively bypass the inherent insulin resistance in dystrophic muscle that may originate from the JNK1 serine phosphorylation of IRS1, thereby limiting dystrophic muscle pathology.

Studies were conducted in which metformin was administered to 4-week old mdx mice followed by extensive biochemical and morphologic analysis. The 4-week age group coincides with the early muscle degeneration/regeneration cycle and as such tests the ability of metformin to limit the degeneration process that begins at 3-4 weeks of age in this murine model of DMD. Metformin delivery was accomplished with the use of osmotic pump technology (Alzet). Alzet osmotic pumps are produced in a variety of formats ideal for use in murine models. The pumps were preloaded with metformin and then surgically implanted in a subcutaneous position suitable for long-term delivery, i.e. mid-scapular region. The Alzet osmotic pump was loaded with a metformin concentration selected to deliver 100 mg/kg/body wt per day, per standard diabetic treatment regimes, at 28 days of continuous infusion (Misra 2008). A skilled person will appreciate that metformin could be given orally or by other routes of administration to humans but the osmotic pump is a convenient way to regulate administration over the 28 days of the murine model. Control animals were implanted with osmotic pumps containing saline. Given that metformin is an anti-hyperglycemic agent, blood glucose levels were measured. Animals were closely monitored and no evidence of hypoglycemia or adverse health effects were observed throughout drug treatment.

As the mechanism of metformin action is known to occur, in part, by directly stimulating AMPK activity (and to a lesser extent AKT activity), AMPK was measured in wild-type and dystrophic muscles (mdx-S, mdx-M). Metformin induced a marked elevation in AMPK kinase activity by 75% (TA) and 55% (DIA) over baseline levels in muscles from mdx-S control (not shown). This confirmed that metformin was active and eliciting a physiological response in dystrophic skeletal muscle.

Example 4

Figure 4:
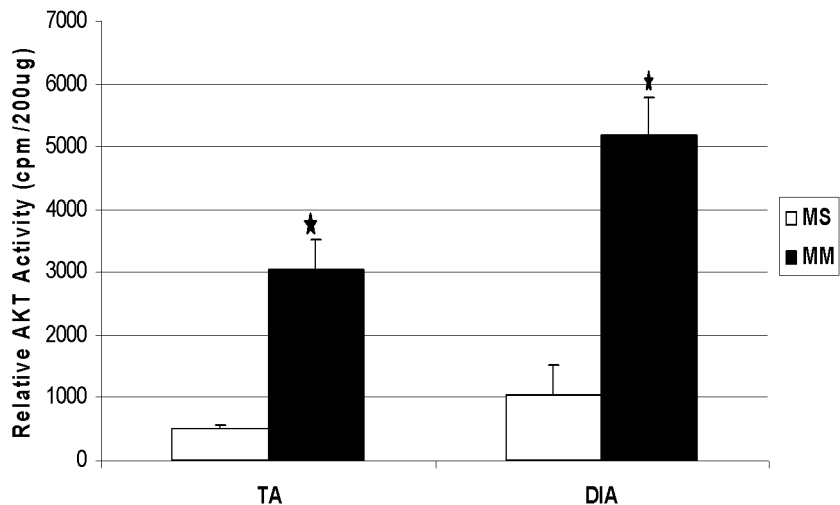
FIG. 4 illustrates that Metformin Treatment Restores Normal AKT phosphorylation and GSK-3β inactivity in Dystrophic Skeletal Muscle. A) Analysis of AKT and GSK-3β kinase activity. AKT was immunoprecipitated from the skeletal muscle (TA and DIA) from MDX-saline (MS) and MDX-metformin treated) mice. AKT kinase assay was preformed using AKT substrate peptide and [γ-32P]ATP. Kinase reaction was dotted on p81 paper and radioactivity was measured by scintillation counter (mean+SE; n>3 *p<0.05). B) Active GSK-3β was immunoprecipitated and GSK-3β kinase assay was preformed using GSK-3β peptide substrate and [γ-32P] ATP. Kinase reaction was dotted on p81 paper and radioactivity was measured by scintillation counter (mean+SE; n>3 *p<0.05).
Figure 4:
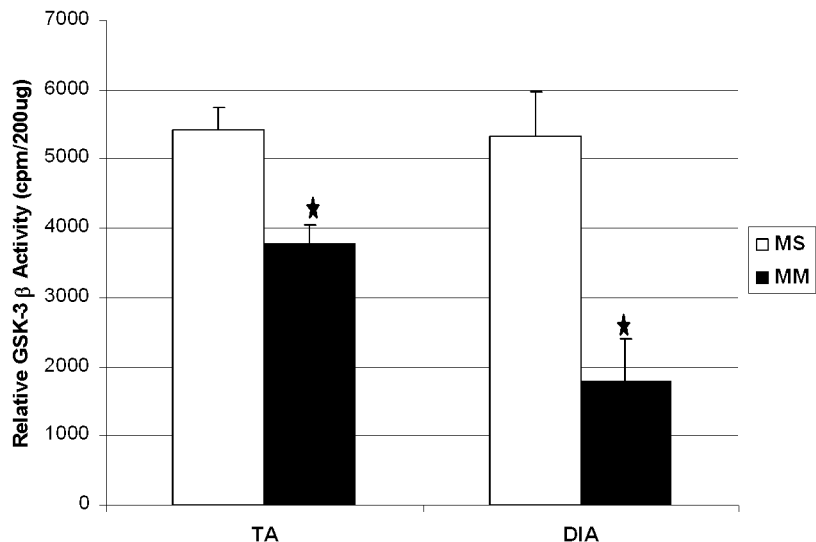

Metformin Rescues Phosphorylation/Activity of Insulin Signaling Intermediates in Dystrophic Muscle Based on the above evidence of impaired insulin-dependent signaling, it was predicted that metformin would improve glucose metabolism independently of IRS-1 phosphorylation. As such, the affects of metformin on insulin signaling intermediates, AKT and GSK-3β, in dystrophic muscle were investigated. Metformin administration in mdx mice led to a substantial increase in skeletal muscle AKT kinase activity in mdx-M (MM) treated muscles compared to mdx-S (MS) control muscles (83% TA and ~80% DIA; FIG. 4A). In addition, GSK-3β activity was significantly reduced by 31% (TA) and 66% (DIA) in mdx-M compared to observations in the mdx-S control group (FIG. 4B). These findings suggest that metformin rescues the activity of the insulin signaling intermediates in dystrophic skeletal muscle.

Example 5

Figure 6:
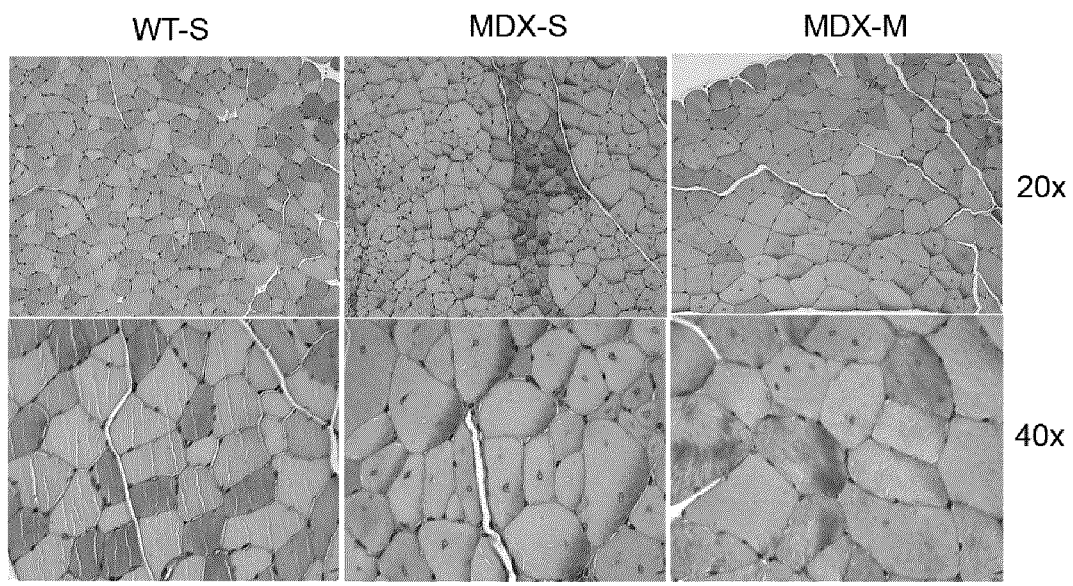
FIG. 6 illustrates that Metformin Treatment Restores Glycogen Content in Dystrophic Skeletal Muscle. Alterations in glycogen storage were analyzed using periodic acid Schiff (PAS) to label glycogen pools on transverse sections of the TA from wild-type (WT) and saline and metformin treated MDX mice, MDX-S and MDX-M respectively. (Magnification, 20× and 40×, n=3).

Metformin Preserves Glycogen Deposition and Enhances GLUT4 Translocation in Dystrophic Muscle The intracellular localization of GLUT4 was measured using immuno-histochemistry and confocal analysis. GLUT4 is the AKT-responsive insulin regulated glucose transporter protein. Metformin administration, in addition to AMPK, has been reported to stimulate glucose uptake by promoting translocation of glucose transporters from intracellular pools to the sarcolemma. In normal healthy skeletal muscle, GLUT4 was localized to discrete regions of the plasma membrane/sarcolemma, along with a diffuse cytoplasmic distribution (FIG. 5, WT-S). However, in mdx dystrophic skeletal muscle, GLUT4 localization was disrupted, as evidenced by minimal sarcolemmal staining, concurrent with a concentrated deposition to vacuolar like structures in the cytoplasm (FIG. 5, MDX-S). Metformin treatment of mdx mice led to a restoration of GLUT4 protein to that observed in wild-type skeletal muscle (FIG. 5, MDX-M). In addition to GLUT4 distribution, the effect of metformin administration on skeletal muscle glycogen levels was also measured. In comparison to wild-type skeletal muscle (FIG. 6, WT-S), mdx skeletal muscle displayed abnormal glycogen deposition, with limited or depleted glycogen content in most fibers and excess glycogen content in a small number of fibers (FIG. 6, MDX-S). These data are consistent with the observations described above that show dystrophic skeletal muscle has enhanced activity of GSK3β (an event that will dramatically impair glycogen deposition through targeted inactivation of glycogen synthase). Subsequently, metformin treatment led to a complete normalization of glycogen content in mdx skeletal muscle (FIG. 6, MDX-M). Taken together, these observations strongly imply that dystrophic skeletal muscle suffers from an inherent metabolic deficiency, arising from inhibition or reduction in insulin-mediated signaling events, and that metformin administration can alleviate this pathology.

Example 6

Metformin Treatment Protects Against Myofiber Degeneration in Dystrophic Muscle

Figure 7:
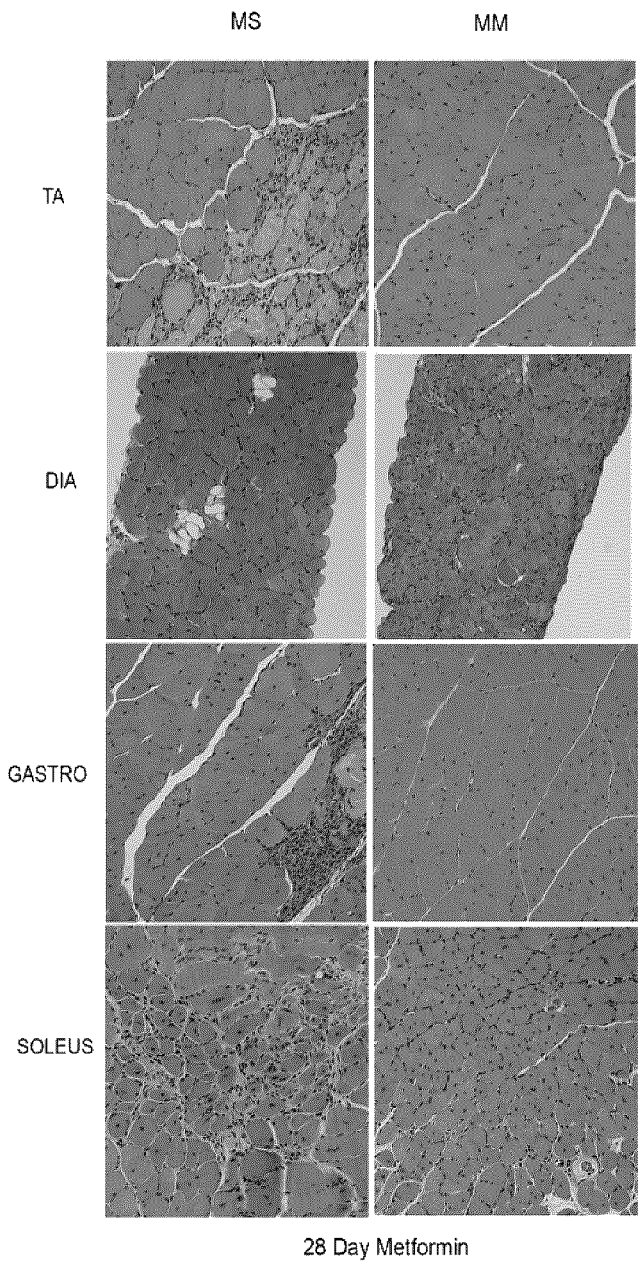
FIG. 7 illustrates that Metformin Treatment Reduces the Appearance of Focal Necrosis in Dystrophic Skeletal Muscle. Following 28 days of metformin administration, the indicated muscles (tibialis anterior [TA], diaphragm [DIA], gastrocnemius [GASTRO] and soleus) were removed, subject to paraffin fixation. Cross-sections from MDX-saline (MS) treated and MDX-metformin (MM) treated mice were stained with H&E to visualize muscle morphology. (Magnification 20×, n=3).

Given that metformin treatment reversed the metabolic deficit in dystrophic skeletal muscle, it was predicted that metformin use may also limit or reverse dystrophic myofiber pathology. Using the same 28-day treatment regime, a dramatic improvement in myofiber pathology was observed following metformin (MM) versus saline (MS) treatment in mdx mice (FIG. 7). Specially, a significant decline in the focal necrosis was noted throughout a number of skeletal muscles, including the TA, DIA, gastrocnemius (GASTRO) and the soleus.

Figure 8:
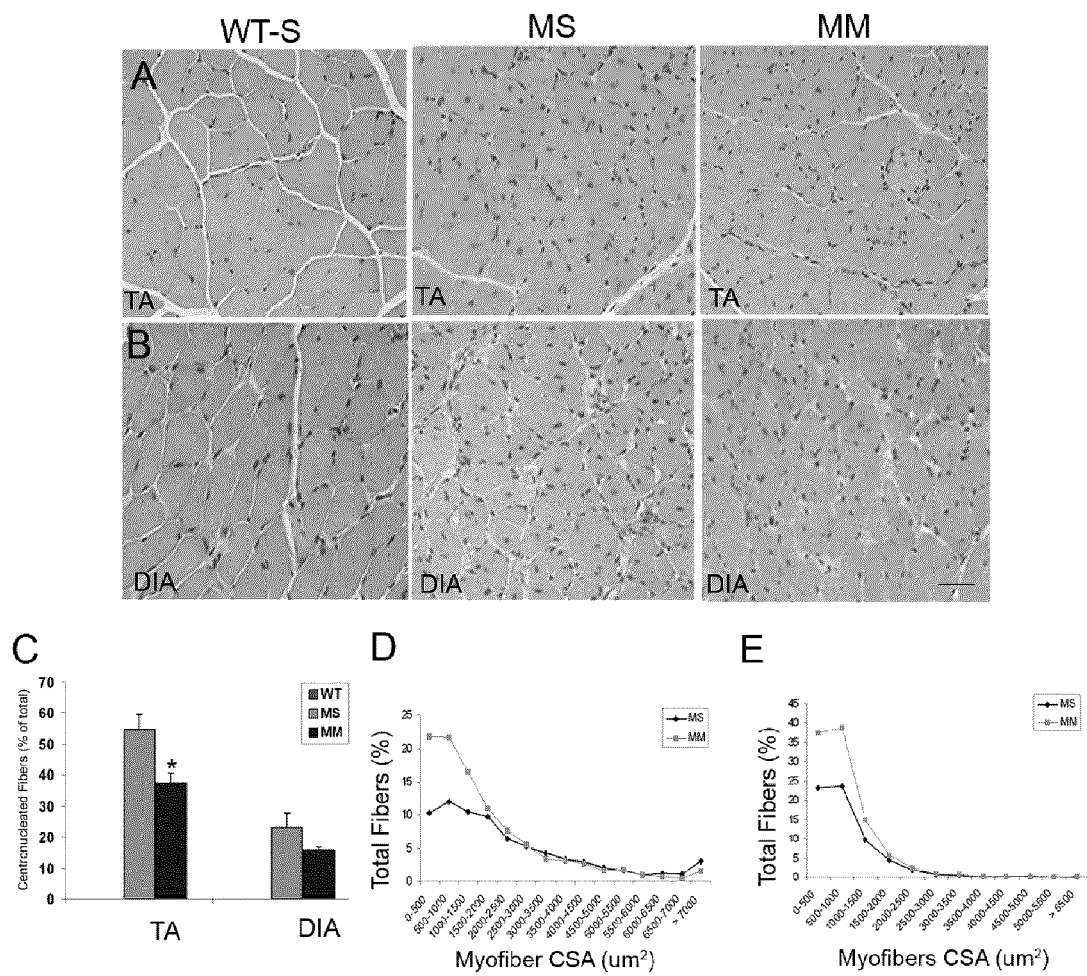
FIG. 8 illustrates that Metformin Treatment Leads to a Reduction in the Number of Centrally Located Myofiber Nuclei in Dystrophic Skeletal Muscle. Following 28 days of metformin administration, the indicated muscles (tibialis anterior [TA] and diaphragm [DIA]) were removed, subject to paraffin fixation. (A-B) cross-sections from TA and DIA in wild-type (WT), MDX-saline (MS) treated and MDX-metformin (MM) treated mice were stained with H&E. (C) Quantification of myofibers with centrally located nuclei (Magnification 20×, n=3). (D-E) Following treatment, metformin treated mdx fibers exhibited a lower proportion of fibres with a smaller cross-sectional area (CSA) compared to saline-treated mdx mice.

In reference to FIG. 8, H & E stained sections on skeletal muscles from WT-S, mdx-S and mdx-M mice were evaluated for analysis of modifications in muscle pathology/morphology. Dystrophic muscle pathology in the mdx strain is characterized by variability in myofiber size with extensive myofiber regeneration (as evidenced by myofibers with centrally located nuclei). Without drug treatment, dystrophic muscles (MS) exhibited a large number of centrally located myonuclei with variable myofiber size compared to wild-type TA and DIA skeletal muscle (FIG. 8 A, B, and illustrated in C). Metformin treatment resulted in a significant reduction in central nuclei with only ~38% of mdx-M dystrophic fibers displaying central nuclei compared to (55%) untreated mdx-S fibers (FIG. 8C). The beneficial effect of metformin in dystrophic muscle was also apparent from analyses of fiber size distribution (based on cross-sectional area). Untreated dystrophic muscles exhibited a greater proportion, 22% (TA) and 38% (DIA), of smaller myofibers (CSA<1500 µm$^2$), whereas mdx-M displayed fewer myofibers, 14% (TA) and 23% (DIA), in the same size range (FIGS. 8 D and E). Similar observations were apparent in other muscles such as gastrocnemius and soleus following metformin treatment (not shown). These findings suggest that metformin treatment provides a protective effect against continual degeneration of muscle fibers, leading to a reduction in the appearance of smaller caliber regenerating myofibers.

Example 7

Metformin Partially Restores the DGC and Improves Myofiber Fragility

Figure 9:
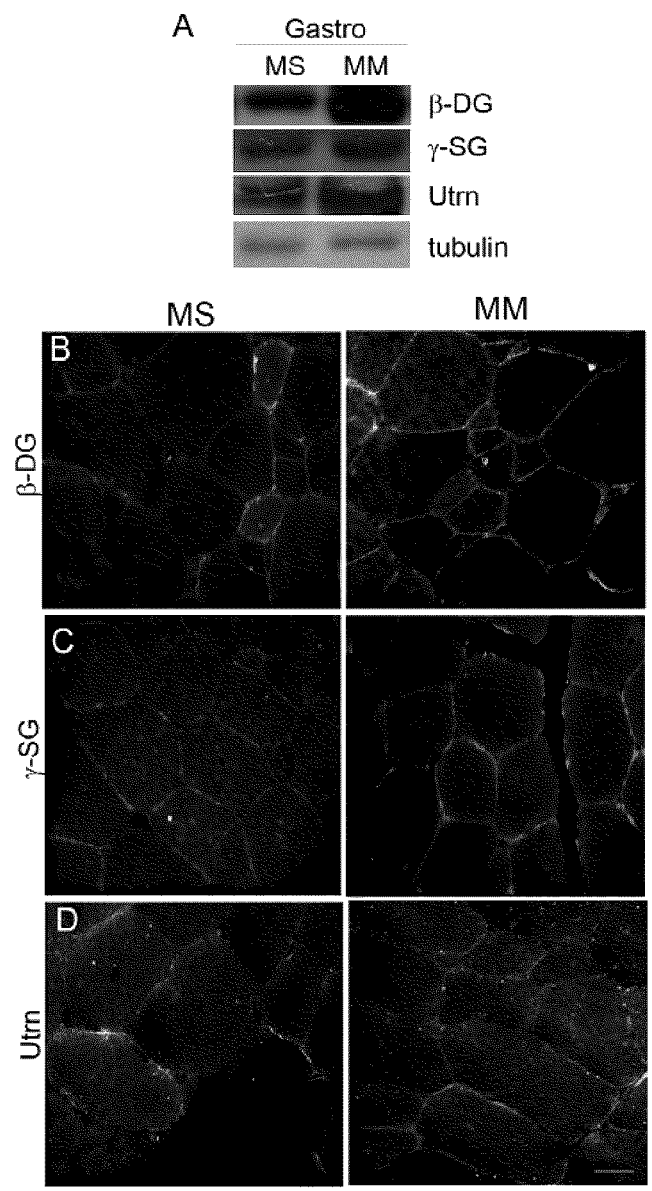
FIG. 9 illustrates that Metformin Partially Restores the DGC and Improves Myofiber Fragility. Metformin administration increased protein levels of utrophin, β-dystroglycan, γ-sarcoglycan and utrophin in the gastrocnemius compared to Saline-treated mdx controls (FIG. 9A). Metformin treatment led to a notable increase in sarcolemmal distribution of both β-dystroglycan and γ-sarcoglycan along the sarcolemma in mdx-myofibers (FIGS. 9B and C). Immunohistochemical analysis revealed that metformin administration led to a robust increase in utrophin along the extrasynaptic sarcolemma (FIG. 9D).

Sarcolemma fragility is commonly known to occur subsequent to the loss of dystrophin/DGC in DMD. Since metformin treatment diminished the degeneration of dystrophic muscle, it was investigated whether the improvement in sarcolemmal integrity was associated with restoration of the DGC. It was found that β-dystroglycan and γ-sarcoglycan protein expression were increased compared to the mdx-Saline (MS) control (FIG. 9A, first and second rows). Similarly, metformin administration increased utrophin protein levels in the gastrocnemius compared to mdx-Saline control (FIG. 9A, third row). Immunohistochemical analysis revealed that metformin treatment led to a notable increase in sarcolemmal distribution of both β-dystroglycan and γ-sarcoglycan along the sarcolemma in mdx-myofibers (FIGS. 9C and C). Similarly, metformin administration led to a robust increase in utrophin along the extrasynaptic sarcolemma (FIG. 9D).

Figure 10:
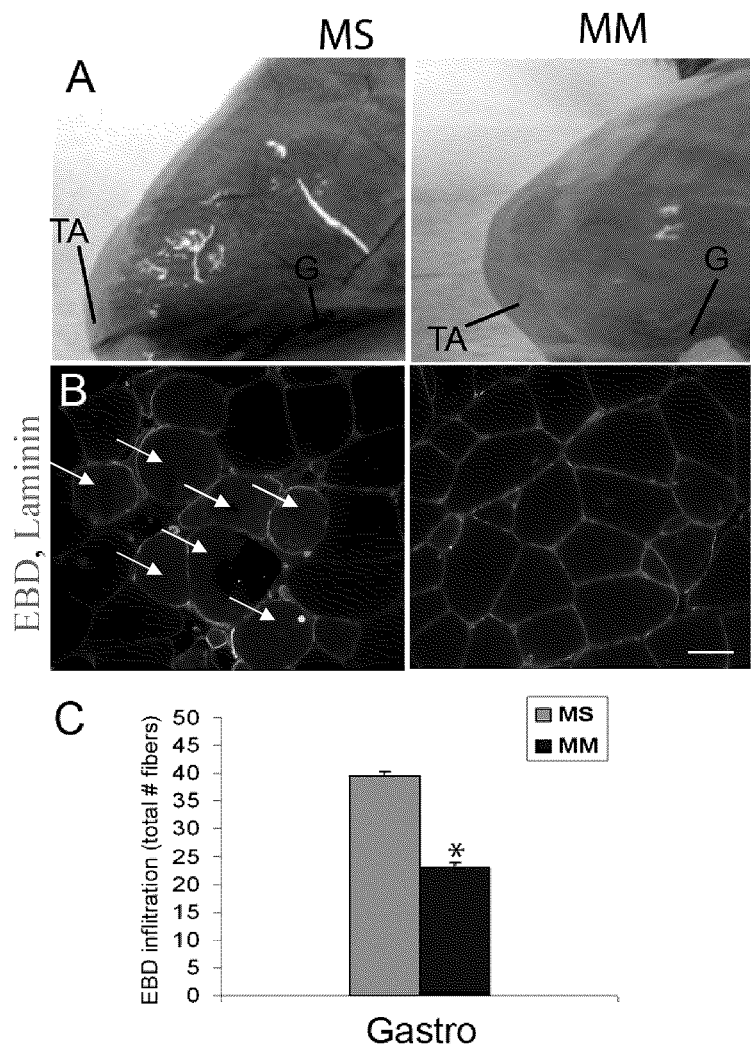
FIG. 10 illustrates that Metformin Treatments decreases sarcolemmal damage in dystrophic skeletal muscle. (A) Macroscopic evidence of EBD infiltration in TA and gastrocnemius (G) muscles from mdx mice treated with saline or metformin for 28 days. (B) Uptake of EBD shown by red fluorescence on transverse sections of gastrocnemius muscle fibres. White arrows indicate muscle fibers that have taken up significant EBD, which fibres appear lighter shade of gray than surrounding fibers in figure. Sarcolemma is visible defining the perimeters of the fibers (scale bar, 20 um). (C) Quantification of EBD-positive fibers. Treated mdx-M (MM) fibers exhibited fewer EBD infiltrated fibers compared to mdx-S (MS). (n=6/group)

The restoration of DGC components suggested that metformin treatment may lead to an improvement in the sarcolemmal fragility of dystrophic skeletal muscle. As such, the infiltration of blood serum albumin into damage muscle fibers bound to the impermeable compound Evans blue dye (EBD) was examined (FIG. 10A). EBD is a standard reagent used in the dystrophy research field to monitor myofiber damage. EBD stained fibers were significantly reduced following metformin treatment compared to mdx-Saline (MS) control (FIG. 10B). Quantification revealed a significant reduction in sarcolemma damage where 42% of untreated (MS) myofibers were positively stained for EBD compared to 22% of treated (MD) fibers (FIG. 10C). Collectively, these results suggest that metformin treatment decreases dystrophic myofiber pathology, in part, by increasing DGC protein content and thereby improving sarcolemmal integrity.

Example 8

Figure 11:
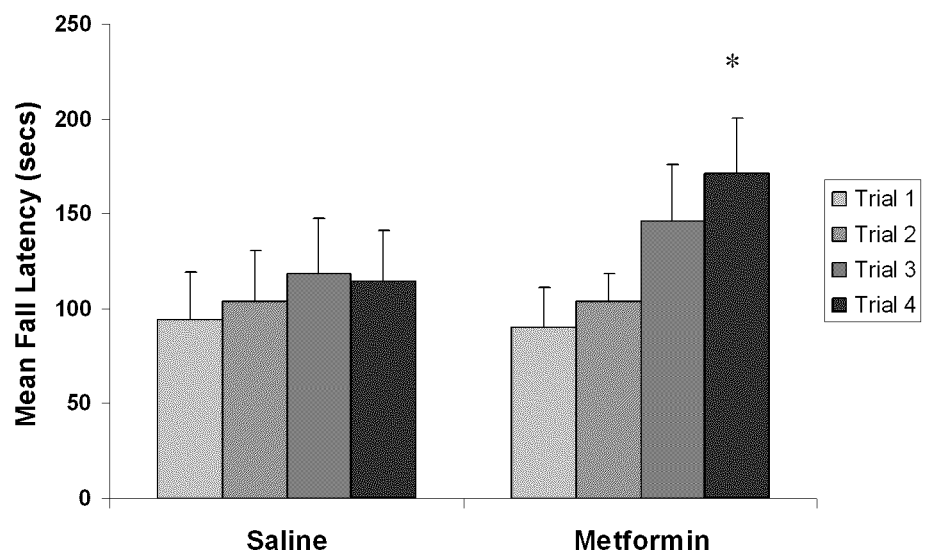
FIG. 11 illustrates the Metformin treated mdx-mice display improved running endurance compared to saline-treated mdx-mice. A) Quantification of fall latency time is represented as the average of each trial (1-4) performed, where each of the 4 trials is performed each day for 3 consecutive days. (n=9±SEM).

Metformin treated mdx-mice display improved motor performance compared to saline-treated mdx-mice. Mice (mdx) 3-4 weeks of age were treated with metformin or saline for 28 days according to the protocol described above. At the end of the treatment phase, a rotorod test was performed, which was repeated daily for 3 consecutive days. The mice were 7-8 weeks of age when tested, thus young adults. The initial rotorod speed for each trial was 15 rpm with gradual acceleration at a rate of 0.1 rpm per second. The results of the study are shown in FIG. 11 (n=9±SEM). Mean fall latency time refers to the average amount of time the mice could run on the rotating rod (seconds). As soon as the animals fell from the rod, the time was stopped. The average value shown represents the average of each trial (1-4) performed for 3 consecutive days. The rotorod test is a behavioural test of motor coordination or performance and fatigue resistance or exercise tolerance, where the earlier time points are essentially an adaptation to the rotorod. The results indicate that, by the 4$^{th}$ trial, the metformin-treated mice successfully adapt to the rotorod with a significant improvement in running time. No comparable improvement was seen in the saline-treated mdx mice. The results indicate that correcting the underlying insulin signalling defect in dystrophic muscle, with metformin treatment, improves motor performance and exercise tolerance (behavioural outcomes) in the diseased animals. This strongly suggests that metformin treatment would alleviate disease pathology in humans suffering from a muscle disease or condition characterized by impaired insulin-dependent signalling.

Example 9

Insulin Treatment does not Limit Dystrophic Myofiber Damage

A study was conducted to determine if insulin itself would alleviate the dystrophic muscle phenotype. It was predicted that insulin would not be as effective as metformin, as both JNK1 activity and IRS-1 phosphorylation would remain elevated thereby blocking the insulin signal (in contrast to metformin which targets insulin signaling intermediates downstream of IRS-1, i.e. effectors of insulin signaling. Dystrophic skeletal muscle showed no significant change in AKT kinase activity and only marginal changes in GSK3β kinase activity following 28-day insulin delivery (not shown). GSK3β kinase activity in insulin-treated mdx mice (mdx-I) was slightly more responsive to insulin. Comparison of myofiber morphology using H & E staining revealed that both TA and DIA fibers of the mdx-I displayed no reduction in fiber size variability and protection against degeneration. Morphometric analysis revealed no overall change in fiber size distribution, in particular the DIA, although a proportion of fibers in the TA of mdx-I were smaller. However, the number of centrally located nuclei remained comparable between mdx-S and mdx-I treatment groups. In addition, GLUT4 remained localized in a perinuclear domain following insulin treatment. These observations confirm that IRS-1/insulin-dependent signaling is impaired in dystrophic muscle and that circumventing this pathway with insulin mimetics such as metformin, which target JNK1 or effectors of insulin signaling downstream of IRS-1, may provide a readily accessible therapy to treat and limit dystrophic muscle damage.

Example 10

Metformin and Corticosteroid Combinatorial Treatment Regime

It was predicted that corticosteroid treatment in combination with metformin treatment would provide an effective combinatorial drug regime to treat muscle disease characterized by impaired insulin-dependent signaling, such as DMD. A study was conducted to assess the impact of prednisolone alone, metformin alone and prednisolone+metformin delivery in the murine mdx model of DMD and the impact on dystrophic muscle pathology.

All drug interventions were tested in both juvenile (3 weeks old) and adult (16 weeks) mdx mice, each drug intervention consisted of 2 subgroups of a 14 day and a 28 day treatment regime (n=7 for each subgroup). The 3 week age group coincides with the early muscle degeneration/regeneration cycle and used to test the ability of each compound to limit the degeneration process, while 16 weeks of age represents a time of decelerated disease progression, which tested the ability of each compound to reverse or limit the existing pathology. As such, the 3 week old mdx treatment group comprised a prednisolone alone group (n=7), a metformin alone group (n=7), a prednisolone/metformin group (n=7), a saline injected control group (n=7) and an osmotic pump/saline control group (n=7). Untreated wild type mice from the same genetic background were also used as additional controls for each treatment regime, for a total of 5 mdx groups (n=35) and 5 wild type groups (n=35) in the juvenile treatment group and a similar number in the adult treatment group (n=70 total). For the prednisolone only treatment regime, prednisolone was administered by intraperitoneal injection every second day at a concentration of 1 uL (approximately 1 mg/kg/day body weight), as in St-Pierre et al. 2004. Metformin delivery was accomplished with the use of osmotic pump technology (Alzet) as described above. Alzet osmotic pumps are produced in a variety of formats ideal for use in murine models. The pumps were preloaded with metformin and then surgically implanted in a subcutaneous position that was suitable for long-term delivery, i.e. mid-scapular region. This enabled delivery of a sustained low dosage over a period of 14 to 28 days at a concentration of 100 mg/kg/day. Daily doses of about 50-150 mg/kg/day may also be administered.

No signs of toxicity were observed in any of the treatment groups.

A variety of individual skeletal muscles will be collected, representing the different fiber constituencies (TA, EDL, soleus, gastrocnemius). Muscles will be analyzed and characterized for baseline metabolic status, the phosphorylation and activity status of insulin signaling components and for standard pathologic indices. Baseline metabolic analysis will include a measure of glycogen distribution using periodic acid Schiff staining on muscle sections and glycogen concentrations through standard biochemical analysis (Megeney et al. 1992) and immuno-localization of the insulin-regulated glucose transporter GLUT4. Skeletal muscle will also be prepared to measure the phosphorylation status of the insulin receptor substrate (IRS-1), and kinase activity for JNK-1, AKT, AMPK and GSK3β, all of which are altered in the dystrophic muscle milieu. Muscle fiber integrity will also be monitored by counting the number of degenerated/regenerated myofibers (central nucleation), myofiber size and immunoglobin infiltration in each of the conditions outlined above. Appropriate statistical analysis will be conducted (ANOVA, posthoc analysis) to determine significance.

Example 11

Preparation of Prodrug $N^1,N^1$-Dimethyl-S-cyclohexyl-$N^4$ Thiohydroxylbiguanidine

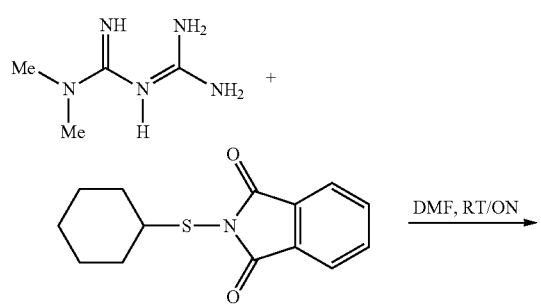

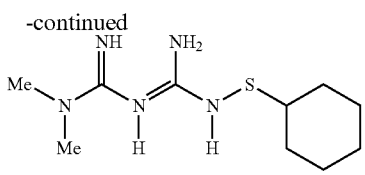

Example 12

In a similar manner $N^1,N^1$-Dimethyl-S-phenyl-$N^4$ thiohydroxylbiguanidine was synthesized.

Example 13

Preparation of tert-Butyl4-[(3 (N,N-Dimethylcarbamimidoyl)guanidino)methyl]phenyl-carbamate

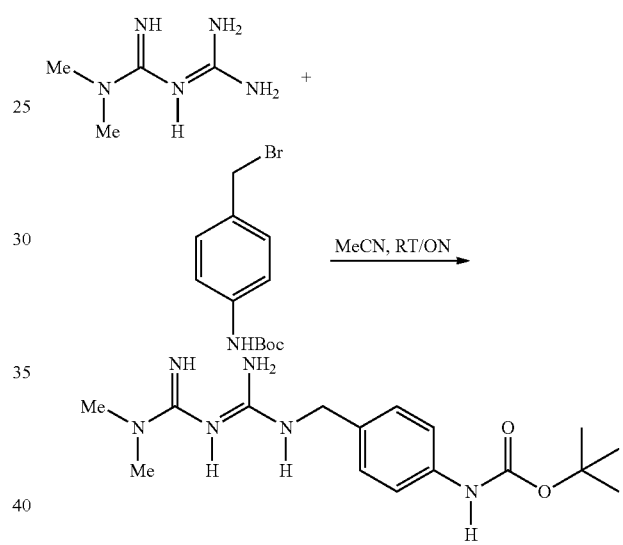

In a similar manner 4-{[3-(N,N-Dimethylcarbamimidoyl) guanidino]methyl}phenyl-octanoate (Example 14) and 4-{[3-(N,N Dimethylcarbamimidoyl)guanidino]methyl}phenyl-diethylcarbamate (Example 15) were synthesized.

Example 16

Preparation of 3-[3-(N,N-Dimethylcarbamimidoyl) guanidino]propyl-acetate

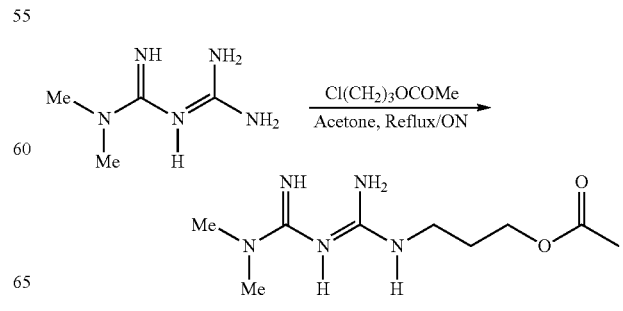

Example 17

Preparation of [(N',N'-Dimethylguanidino)iminomethyl]carbamic acid benzyl-ester

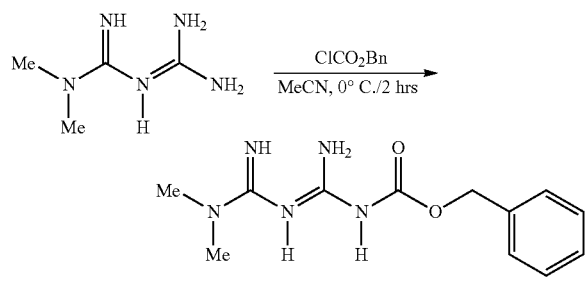

Example 18

In a similar manner [(N',N'-Dimethylguanidino)iminomethyl]carbamic acid 2,2,2-Trichloroethyl-ester.

Example 19

Preparation of [($N^1$,$N^1$-Dimethylcarbamimidoyl)guanidino]-4-phenyl-1,3,2-dioxaphosphoramidate

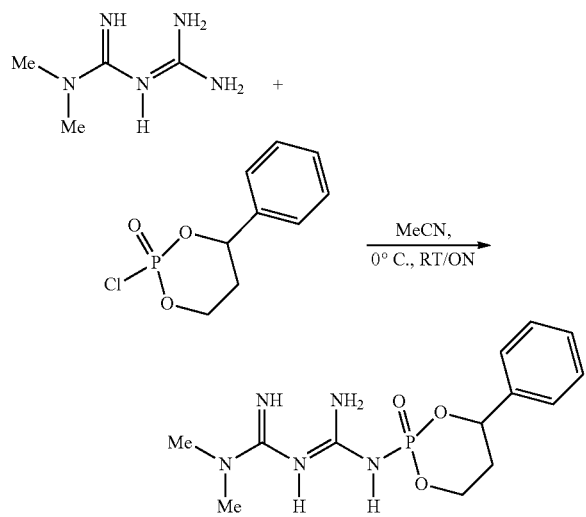

Materials and Methods

Animal Models.

Wild-type (C57BL-10) and mdx mice (C57BL/10ScSn-DMD/$^{mdx}$) were purchased from Jackson Laboratories (Bar Harbour, Me.) and housed in the University of Ottawa Animal Care Facility. Mice aged 3-4 weeks (peak necrotic stage) were surgically implanted with an (Alzet) osmotic minipump containing metformin or insulin for 14 and 28 days. Animals were randomly assigned to experimental or control treatment groups. Depending on the experiment, Mdx mice either received 100 mg/kg/d of metformin (Aldrich) (mdx-M) or 0.75 U of insulin (Sigma) (mdx-I). Drug concentrations were based on the effective dose range used in diabetic mouse models (Bailey and Puah, 1986; Cohen et al., 2004)

Control groups were surgically implanted with the minipump containing saline (wild type [WT-S], mdx-S). Following completion of drug treatment, animals were sacrificed by cervical dislocation and skeletal muscles (tibialis anterior TA, diaphragm DIA, gastrocnemius Gastro, and Soleus) were harvested. For analysis of biochemistry, skeletal muscles were snap frozen in liquid nitrogen. For preparation of paraffin sections skeletal muscles were fixed in formalin.

Immunofluorescence.

Paraffin embedded muscles were section transversely (10 ☐m) and deparaffinized in descending alcohols, blocked with 3% BSA and permeabilized in 0.1% triton in PBS for 1 h at RT. Sections were then incubated in primary antibodies against GLUT4 (Chemicon), Laminin (Sigma), Utrophin, 13-Dystroglycan and γ-Sarcoglycan were purchased from Vector Laboratories. In order to amplify primary antibody signal the avidin/biotin complex technique was performed on muscle sections. As well primary mouse antibodies were diluted in M.O.M diluent (M.O.M. Basic Kit, Vector Laboratories). In brief, sections were incubated with primary antibody overnight at 4° C. then incubated in biotinylated secondary antibody for 30 mins at RT, followed by incubation in FITC-streptoavidin conjugated secondary antibody (Molecular Probes) for 1 h at RT. Sections were then washed and mounted using fluorescence mounting medium (DAKO).

Histological Analysis

Hematoxylin and Eosin (H&E).

Muscle sections were rehydrated in xylene followed by descending alcohols (100%, 95%, 80%), incubated in Shandon Instant Hematoxylin (Fisher Scientific) for 3 mins, washed 1 min, incubated in Eosin (Fisher Scientific) for 3 mins and then dehydrated in ascending alcohols followed by incubation in xylene. Stained sections were mounted with permount (Fisher Scientific). Quantification of morphometric parameters was performed on ~1000 fibers per muscle.

Periodic Acid Schiff (PAS).

To measure glycogen deposition deparaffinized, rehydrated muscle sections were stained according to manufacturer's instructions (Periodic Acid Schiff Staining Kit; Polysciences, Inc). Briefly, muscle sections were incubated in 0.5% periodic acid for 5 mins, washed, incubated in Schiff's reagent for 15 mins, and then rinsed in 0.55% potassium metabisulfite. Next sections were counterstained with hematoxylin, washed, dehydrated in ascending alcohols and then mounted with permount (Fisher Scientific).

Evans Blue Dye.

To measure sarcolemmal integrity, treated and untreated mdx mice were injected intravenously through the dorsal tail vein with 50 ul/10 g of 1% Evans Blue Dye (EBD, Sigma) in sterilized phosphate-buffered saline (PBS 7.4). Skeletal muscle was harvested 6-8 hrs post-injection and prepared for immunofluorescence as previously described. To visualize sarcolemmal membrane, EBD infiltrated fibers sections were incubated in anti-laminin (Sigma) at 4° C. overnight and then mounted in fluorescent mounting medium (DAKO).

Immunoblot Analysis.

Muscle samples were homogenized, lyzed and quantified for protein concentration using Brafford Assay. Equal concentrations of protein samples were resolved by 6-8% SDS-PAGE and transferred to nitrocellulose membranes. Primary antibodies against IRS, IRS$^{y941}$, IRS$^{S307}$, anti-MHC (clone MF20) were used at a dilution of 1:500. Rabbit polyclonal antibodies were detected using horseradish peroxidase-conjugated anti-rabbit at dilution of 1:5000. Immunoblots were developed using with Supersignal West Pico Chemiluminescence substrate.

Kinase Activity Assay.

Muscle samples were homogenized and quantified for protein concentration using Brafford Assay. Equal concentrations of protein samples were immunoprecipitated for AKT and GSK3-β overnight at 4° C. Sepharose beads containing the immunoprecipitated AKT or GSK3-b were washed and then incubated in reaction buffer a specific peptide substrate ARKRERTYSFGHHA and RRRPAS-VPPSPSLSRHSSHQRR, respectively with [γ-$^{32}$P]-ATP at 37° C. After incubation, beads were pelleted and equal amounts of supernatant was spotted on p-81 phosphocellulose paper, washed in phosphoric acid, then washed in acetone and air-dried. Incorporation of radioactivity was counted using liquid scintillation counter.

Immunoprecipitation and Kinase Activity Assay

Muscle samples were prepared and 200 μg of total protein was incubated with specific antibodies against AMPK, AKT, and GSK-3β overnight at 4° C. Protein G sepharose beads (Amersham Biosciences) were then added to the lysates and rotated for 4 hr at 4° C. The lysate-bead mixture was clarified by centrifugation at 1100 rpm for 1 min and prepared for kinase reaction as described below. The immunoprecipitated beads were washed twice with modified RIPA lysis buffer and once in kinase buffer: (100 mmol/L MOPS pH 7.2, 125 mmol/L β-glycerol phosphate, 25 mmol/L EGTA, 5 mmol/L sodium orthovanadate, and 5 mmol/L DTT) for AKT kinase activity and 50 mM Tris/HCL pH 7.5, 0.1 mM EGTA, 0.1% (by volume) 2-mercoptoethanol, 10 mM magnesium acetate for the AMPK kinase assay. The kinase buffer for GSK-3β assay consisted of 25 mmol/L HEPES pH 7.4, 10 mmol/L MgCl$_2$, and 1 mmol/L DTT. Immunoprecipitates were then incubated in the specific kinase buffer supplemented with [γ-$^{32}$P]ATP and either RPRAATF (including PKA inhibitor peptide from Akt1/PKBα immunoprecipitation kinase assay; Upstate Biotechnology), YRRAAVPPSPSLSRHSSPHQPS (Upstate, Biotechnology) or SAMS (Upstate, Biotechnology) peptides as target substrates for AKT/SGK, GSK3-β and AMPK, respectively. After incubation at 37° C. for 20-30 mins, beads were pelleted and equal amounts of supernatant was spotted on P81 phosphocellulose squares (Upstate, Biotechnology). Papers were washed twice in 0.75% phosphoric acid, acetone and air-dried. Incorporation of radioactivity was counted using a liquid scintillation counter and expressed as counts per minute (cpm) per 200 microgram of protein.

Viewing and Imaging.

H & E stained muscle sections were viewed using brightfield light microscopy on a Nikon Eclipse 80i microscope (Nikon Instruments, Inc). To image immunofluorescence muscle, sections were analyzed using Axioplan 2 fluorescent microscope with appropriate filters. Images were created using Axiovision 4.5 software (Carl Zeiss, Inc).

Statistics.

All data are expressed as mean±SEM. Statistical significance was determined using two-tailed Student's t test, statistical significance defined as $*p<0.05$.

ABBREVIATIONS

AMPK AMP (adenosine monophosphate)-activated protein kinase
atm Atmosphere
aq. Aqueous
BINAP 2,2'-bis(diphenylphosphino)-1,1'-binaphthyl
Boc tert-butoxycarbonyl
CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIA Diaphragm
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EA Ethyl acetate
EBD Evans blue dye
EDCI N-[3-(dimethylamino)propyl]-N'-ethylcarbodiimide hydrochloride
EDC 1-Ethyl-3-(3-dimethylaminopropyl)carbodiimide
Et$_2$O Diethylether
EtOAc Ethyl acetate
EtOH Ethanol
EtI Iodoethane
Et Ethyl
Fmoc 9-fluorenylmethyloxycarbonyl
GLUT4 glucose transporter type 4
GP Protecting group
GS Glycogen synthase
GSK3β Glycogen synthase kinase 3β
h hour(s)
HetAr Heteroaryl
HOBt N-Hydroxybenzotriazole
HBTU O-(Benzotriazol-1-yl)-N,N,N',N'-tetramethyluronium hexafluorophosphate
HPLC High performance liquid chromatography
IRS-1 Insulin receptor substrate-1
JNK-1 Jun kinase 1
LAH Lithium aluminium hydride
LCMS HPLC mass spec
MCPBA m-Chlorbenzoic acid
MeCN Acetonitrile
MeOH Methanol
min Minutes
MeI Iodomethane
MeMgCl Methyl magnesium chloride
Me Methyl
MM metformin-treated mdx mice (also M-mdx, Met-mdx or mdx-Met, etc)
n-BuLi 1-Butyllithium
NaOAc Sodium acetate
NMR Nuclear magnetic resonance
NMP N-Methyl pyrrolidinone
nBuLi 1-Butyl lithium
o.n. Over night
PI 3 kinase phosphatidylinositol 3-kinase
RT, rt, r.t. Room temperature
TEA Triethylamine
THF Tetrahydrofurane
nBu normal Butyl
OMs Mesylate or methane sulfonate ester
OTs Tosylate, toluene sulfonate or 4-methylbenzene sulfonate ester
PCC Pyridinium chlorochromate
PIP$_3$ Phosphatidylinositol (3,4,5)-triphosphohate
PPTS Pyridinium p-toluenesulfonate
TA Tibialis anterior
TBAF Tetrabutylammonium fluoride
pTsOH p-Toluenesulfonic acid
SPE Solid phase extraction (usually containing silica gel for mini-chromatography)
sat. Saturated SM saline-treated mdx mice (also S-mdx, Sal-mdx or mdx-Sal, etc)
WT Wild-type

REFERENCES

Abramovici, H., Hogan, A. B., Obagi, C., Topham, M. K., and Gee, S. H. (2003). Diacylglycerol kinasezeta localization in skeletal muscle is regulated by phosphorylation and interaction with syntrophins. *Mol Biol Cell.* 14, 4499-4511.

Aguirre, V., Uchida, T., Yenush, L., Davis, R., and White, M. F. (2000). The c-Jun NH(2)-terminal kinase promotes insulin resistance during association with insulin receptor substrate-1 and phosphorylation of Ser(307). *J Biol Chem.* 275, 9047-9054.

Bailey C J, Puah J A (1986) Effect of metformin on glucose metabolism in mouse soleus muscle. Diabete Metab 12: 212-8.

Bundgaard H, ed., New York: Elsevier; 1985: 93-133

Barton, E. R., Morris, L., Musaro, A., Rosenthal, N., Sweeney, H. L. (2002). Muscle-specific expression of insulin-like growth factor I counters muscle decline in mdx mice. *J Cell Biol.* 157, 137-148.

Barton, E. R. (2006). The ABCs of IGF-I isoforms: impact on muscle hypertrophy and implications for repair. *Appl Physiol Nutr Metab.* 31, 791-797. Review.

Blaauw, B., Mammucari, C., Toniolo, L., Agatea, L., Abraham, R., Sandri, M., Reggiani, C., Schiaffino, S. (2008). Akt activation prevents the force drop induced by eccentric contractions in dystrophin-deficient skeletal muscle. Hum Mol Genet. 17, 3686-3696.

Chakkalakal, J. V., Harrison, M. A., Carbonetto, S., Chin, E., Michel, R. N., and Jasmin, B. J. (2004). Stimulation of calcineurin signaling attenuates the dystrophic pathology in mdx mice. *Hum Mol Genet.* 13, 379-388.

Chakkalakal, J. V., Thompson, J., Parks, R. J., and Jasmin, B. J. (2005). Molecular, cellular, and pharmacological therapies for Duchenne/Becker muscular dystrophies. *FASEB J.* 19, 880-891. Review.

Chakkalakal, J. V., Michel, S. A., Chin, E. R., Michel, R. N., and Jasmin, B. J. (2006). Targeted inhibition of Ca2+/calmodulin signaling exacerbates the dystrophic phenotype in mdx mouse muscle. *Hum Mol Genet.* 15, 1423-1435.

Chen, Y. W. Zhao, P., Borup, R., and Hoffman, E. P. (2000). Expression profiling in the muscular dystrophies: identification of novel aspects of molecular pathophysiology. *J Cell Biol.* 151, 1321-1336.

Chin, E. R., Olson, E. N., Richardson, J. A., Yang, Q., Humphries, C., Shelton, J. M., Wu, H., Zhu, W., Bassel-Duby, R., and Williams, R. S. (1998). A calcineurin-dependent transcriptional pathway controls skeletal muscle fiber type. *Genes Dev.* 12, 2499-2509.

Cho D H. et al., Myotonic dystrophy: emerging mechanisms for DM1 and DM2, *Biochim Biophys Acta.* 2007 1772(2): 195-204

Chung, J., Nguyen, A. K., Henstridge, D. C., Holmes, A. G., Chan, M. H., Mesa, J. L., Lancaster, G. I., Southgate, R. J., Bruce, C. R., Duffy, S. J., Horvath, I., Mestril, R., Watt, M. J., Hooper, P. L. Kingwell, B. A., Vigh, L., Hevener, A., and Febbraio, M. A. (2008). HSP72 protects against obesity-induced insulin resistance. *Proc Natl Acad Sci USA.* 105, 1739-1744.

Cohen S E, Tseng Y H, Michael M D, Kahn C R (2004) Effects of insulin-sensitising agents in mice with hepatic insulin resistance. Diabetologia 47:407-11.

Ervasti, J. M., and Sonnemann, K. J. (2008). Biology of the striated muscle dystrophin-glycoprotein complex. *Int Rev Cytol.* 265, 191-225. Review.

Even, P. C., Decrouy, A., and Chinet, A. (1994). Defective regulation of energy metabolism in mdxmouse skeletal muscles. *Biochem J.* 304, 649-654.

Freund A A. et al., Arg. Neuro Arg. Neuropsidiatr. 2007, 65(1):73-6

Gregorevic, P., Plant, D. R., Lynch, G. S. (2004). Administration of insulin-like growth factor-I improves fatigue resistance of skeletal muscles from dystrophic mdx mice. *Muscle Nerve.* 30, 295-304.

Guglieri M. et al., Limb-Girdle muscular dystrophies. Curr Opin Neurol., 2008, 21(5): 576-84

Hasegawa, M., Cuenda, A., Spillantini, M. G., Thomas, G. M., Buee-Scherrer, V., Cohen, P., and Goedert, M. (1999). Stress-activated protein kinase-3 interacts with the PDZ domain of alpha1-syntrophin. A mechanism for specific substrate recognition. *J Biol Chem.* 274, 12626-12631.

Hilder, T. L., Tou, J. C., Grindeland, R. E. Wade, C. E., Graves, L. M. (2003). Phosphorylation of insulin receptor substrate-1 serine 307 correlates with JNK activity in atrophic skeletal muscle. *FEBS Lett.* 553, 63-67.

Hirosumi, J., Tuncman, G., Chang, L., Gorgun, C. Z., Uysal, K. T., Maeda, K., Karin, M., Hotamisilgil, G. S. (2002). A central role for JNK in obesity and insulin resistance. *Nature.* 420, 333-336.

Han, Hyo-Kyung, AAPS Pharmsci. 2000, 2(1) article 6.

Huttunen K M. et al., *J. Med. Chem.* 2009, 52, (14):4142-8,

Huttunen K M. et al., *Synthesis* 2008, 22, 3619-3624

Khairallah, M., Khairallah, R., Young, M. E., Dyck, J. R., Petrof, B. J., Des Rosiers, C. (2007). Metabolic and signaling alterations in dystrophin-deficient hearts precede overt cardiomyopathy. *J Mol Cell Cardiol.* 43, 119-129.

Langenbach, K. J., and Rando, T. A. (2002). Inhibition of dystroglycan binding to laminin disrupts the PI3K/AKT pathway and survival signaling in muscle cells. *Muscle Nerve.* 26, 644-653.

Liguori C L. et al., Myotonic dystrophy type 2 caused by a CCTG expansion in intron 1 of ZNF9. Science. 2001 3; 293(5531): 864-7

Lizcano, J. M., and Alessi, D. R. (2002). The insulin signalling pathway. *Curr Biol.* 12, R236-238. Review.

Lumeng, C., Phelps, S., Crawford, G. E., Walden, P. D., Barald, K., and Chamberlain, J. S. (1999). Interactions between beta 2-syntrophin and a family of microtubule-associated serine/threonine kinases. *Nat Neurosci.* 2, 611-617.

Nogrady (1985) *Medicinal Chemistry A Biochemical Approach*, Oxford University Press, New York, pages 388-392.

Madhavan, R., and Jarrett, H. W. (1994). Calmodulin-activated phosphorylation of dystrophin. *Biochemistry.* 33, 5797-5804.

Madhavan, R., and Jarrett, H. W. (1999). Phosphorylation of dystrophin and alpha-syntrophin by Ca(2+)-calmodulin dependent protein kinase II. *Biochim Biophys Acta.* 1434, 260-274.

Misra, P. (2008). AMP activated protein kinase: a next generation target for total metabolic control. *Expert Opin Ther Targets.* 12, 91-100. Review.

Mokhtarian, A., Decrouy, A., Chinet, A., and Even, P. C. (1996). Components of energy expenditure in the mdx mouse model of Duchenne muscular dystrophy. *Pflugers Arch.* 431, 527-532.

Musaro, A., McCullagh, K. J., Naya, F. J., Olson, E. N., and Rosenthal, N. (1999). IGF-1 induces skeletal myocyte hypertrophy through calcineurin in association with GATA-2 and NF-ATc1. *Nature.* 400, 581-585.

Musi N, Hirshman M F, Nygren J, Svanfeldt M, Bavenholm P, Rooyackers O, Zhou G, Williamson J M, Ljunqvist O, Efendic S, Moller D E, Thorell A, Goodyear L J. (2002). Metformin increases AMP-activated protein kinase activity in skeletal muscle of subjects with type 2 diabetes. *Diabetes.* 51, 2074-2081.

Musi N, Goodyear L J. (2006). Insulin resistance and improvements in signal transduction. *Endocrine.* 29, 73-80. Review.

Naya, F. J., Mercer, B., Shelton, J., Richardson, J. A., Williams, R. S., Olson, E. N. (2000). Stimulation of slow skeletal muscle fiber gene expression by calcineurin in vivo. *J Biol Chem.* 275, 4545-4548.

Noguchi, S. (2005). The biological function of insulin-like growth factor-I in myogenesis and its therapeutic effect on muscular dystrophy. *Acta Myol.* 24, 115-118. Review.

Peter, A. K., Ko, C. Y., Kim, M. H, Hsu, N., Ouchi, N., Rhie, S., Izumiya, Y., Zeng, L., Walsh, K., Crosbie, R. H. (2009). Myogenic Akt signaling upregulates the utrophin-glycoprotein complex and promotes sarcolemma stability in muscular dystrophy. Hum Mol. Genet. 18, 318-327.

Petrof, B. J., Shrager, J. B., Stedman, H. H., Kelly, A. M., and Sweeney, H. L. (1993). Dystrophin protects the sarcolemma from stresses developed during muscle contraction. *Proc Natl Acad Sci USA.,* 90, 3710-3714.

St-Pierre, S. J. G., Kolodziejczyk, S. M., Knudson, J. C., Chakkallal, J., Jasmin, B., and Megeney L A. (2004). Glucocorticoid treatment alleviates dystrophic myofiber pathology by activation of the calcineurin/NF-AT pathway. *FASEB J.* 18, 1937-1939.

Sandri, M., Sandri, C., Gilbert, A., Skurk, C., Calabria, E., Picard, A., Walsh, K., Schiaffino, S., Lecker, S. H., and Goldberg, A. L. (2004). Foxo transcription factors induce the atrophy-related ubiquitin ligase atrogin-1 and cause skeletal muscle atrophy. *Cell.* 117, 399-412.

Semsarian, C., Wu, M. J., Ju, Y. K., Marciniec, T., Yeoh, T., Allen, D. G., Harvey, R. P., and Graham, R. M. (1999). Skeletal muscle hypertrophy is mediated by a Ca2+-dependent calcineurin signaling pathway. *Nature.* 400, 576-581.

Sewry C A., J Muscle Res Cell Motil. 2008, 29(6-8):231-8

Schertzer, J. D., and Lynch, G. S. (2006). Comparative evaluation of IGF-I gene transfer and IGF-I protein administration for enhancing skeletal muscle regeneration after injury. *Gene Ther.* 13, 1657-1664.

Schertzer, J. D., Ryall, J. G., and Lynch, G. S. (2006). Systemic administration of IGF-I enhances oxidative status and reduces contraction-induced injury in skeletal muscles of mdx dystrophic mice. *Am J Physiol Endocrinol Metab.* 291, E499-E505.

Stella V J, et al. *Drugs.* 1985, 29:455-473

Stebbins et al, 2008 PNAS, October 28, vol 105 (43), p. 16809-16813.

Stitt, T. N., Drujan, D., Clarke, B. A., Panaro, F., Timofeyva, Y., Kline, W. O. Gonzalez, M., Yancopoulos, G. D., Glass, D. J. (2004). The IGF-1/PI3K/Akt pathway prevents expression of muscle atrophy-induced ubiquitin ligases by inhibiting FOXO transcription factors. *Mol Cell.* 14, 395-403.

Stupka, N., Plant, D. R., Schertzer, J. D., Emerson, T. M., Bassel-Duby, R., Olson, E. N., and Lynch, G. S. (2006). Activated calcineurin ameliorates contraction-induced injury to skeletal muscles of mdx dystrophic mice. *J Physiol.* 575, 645-656.

Stupka, N., Schertzer, J. D., Bassel-Duby, R., Olson, E. N., and Lynch, G. S. (2008). Stimulation of calcineurin A{alpha} activity attenuates muscle pathophysiology in mdx dystrophic mice. *Am J Physiol Regul Integr Comp Physiol.* 294, R983-R992.

Suwa M, Egashira T, Nakano H, Sasaki H, Kumagai S. (2006). Metformin increases the PGC-1alpha protein and oxidative enzyme activities possibly via AMPK phosphorylation in skeletal muscle in vivo. *J Appl Physiol.* 101, 1685-1692.

Tawil R. Facioscapulohumeral muscular dystrophy. Neurotherapeutics. 2008 5(4):601-6

Vainzof M, et al., J Mol Neurosci. 2008, 34(3):241-8

Wu, H., Naya, F. J., McKinsey, T. A., Mercer, B., Shelton, J. M., Chin, E. R., Simard, A. R., Michel, R. N., Bassel-Duby, R., Olson, E. N., and Williams, R. S. (2000). MEF2 responds to multiple calcium regulated signals in the control of skeletal muscle fiber type. *EMBO J.* 19, 1963-1973.

Yang, B., Jung, D., Motto, D., Meyer, J., Koretzky, G., and Campbell, K. P. (1995). SH3 domain mediated interaction of dystroglycan and Grb2. *J Biol Chem.* 270, 11711-11714.

Zhou G, Myers R, Li Y, Chen Y, Shen X, Fenyk-Melody J, Wu M, Ventre J, Doebber T, Fujii N, Musi N, Hirshman M F, Goodyear L J, Moller D E. (2001). Role of AMP-activated protein kinase in mechanism of metformin action. *J Clin Invest.* 108, 1167-1174.

The above-described embodiments are intended to be examples only. Alterations, modifications and variations can be effected to the particular embodiments by those of skill in the art without departing from the scope of the invention, which is defined solely by the claims appended hereto.

The invention claimed is:

1. A method of treating a muscle disease or condition comprising administering to a subject in need thereof a therapeutically effective amount of a therapeutic agent that is metformin or an analog or derivative thereof, wherein the muscle disease or condition is Duchenne muscular dystrophy.

2. The method of claim 1, wherein the therapeutic agent is administered orally or parenterally.

3. The method of claim 1, wherein the therapeutic agent is administered parenterally.

4. The method of claim 3 wherein the parenteral administration is intramuscular, intravenous, or intraarterial.

5. The method of claim 1, further comprising administering a corticosteroid to the subject.

6. The method of claim 5, wherein the corticosteroid is prednisone, prednisolone, deflazacort, dexamethasone, or a combination thereof.

7. The method of claim 5, wherein the therapeutic agent is metformin and the corticosteroid is prednisolone.

8. A method of treating a muscle disease characterized by impaired insulin-dependent signaling comprising administering to a patient a therapeutically effective amount of metformin, wherein the muscle disease is Duchenne muscular dystrophy.

* * * * *